United States Patent [19]
Dennis et al.

[11] Patent Number: 5,863,893
[45] Date of Patent: Jan. 26, 1999

[54] FACTOR VIIA INHIBITORS FROM KUNITZ DOMAIN PROTEINS

[75] Inventors: Mark S. Dennis, San Carlos; Robert A. Lazarus, Millbrae, both of Calif.

[73] Assignee: Genentech, Inc., San Francisco, Calif.

[21] Appl. No.: 398,628

[22] Filed: Mar. 3, 1995

Related U.S. Application Data

[63] Continuation-in-part of Ser. No. 206,310, Mar. 4, 1994.
[51] Int. Cl.$^6$ .......................... A61K 38/55; A61K 38/57; C07K 14/81; C12N 9/64
[52] U.S. Cl. ............................ 514/12; 435/226; 514/822; 930/250
[58] Field of Search .......................... 514/2, 12; 530/300, 530/324, 350; 435/69.2, 226; 930/250

[56] References Cited

U.S. PATENT DOCUMENTS

| | | | |
|---|---|---|---|
| 4,894,436 | 1/1990 | Auerswald et al. | 530/324 |
| 5,032,573 | 7/1991 | Auerswald et al. | 514/12 |
| 5,223,482 | 6/1993 | Schilling, Jr. et al. | 514/12 |
| 5,455,338 | 10/1995 | Sprecher | 536/23.5 |

FOREIGN PATENT DOCUMENTS

| | | |
|---|---|---|
| 0339942 | 11/1989 | European Pat. Off. . |
| 393431 | 10/1990 | European Pat. Off. . |
| 9314123 | 7/1993 | WIPO . |
| WO 93/14119 | 7/1993 | WIPO . |
| WO 93/14120 | 7/1993 | WIPO . |
| WO 93/14121 | 7/1993 | WIPO . |
| WO 93/14122 | 7/1993 | WIPO . |
| WO 93/14123 | 7/1993 | WIPO . |
| WO 94/01461 | 1/1994 | WIPO . |

OTHER PUBLICATIONS

Badimon et al., "Hirudin and Other Thrombin Inhibitors; Experimental Results and Potential Clinical Applications" *TCM* 1 (6):261–267 (1991).

Beckmann et al, "Preparation of chemically 'mutated' aprotinin homologues by semisynthesis p1 substitutions change inhibitory specificity" *J. Biochem.* 176(FEBS) :675–682 (1988).

Bigler et al., "Binding of amino acid side chains to preformed cavities: Interaction of serine proteinases with turkey ovomucoid third domains with coded and noncoded P1 residues" *Prot. Sci.* 2:786–799 (1993).

Bode et al., "Natural protein proteinase inhibitors and their interaction with proteinases" *European Journal of Biochemistry* 204:433–451 (1992).

Broze Jr., et al., "Inhibition of Factor VIIa/Tissue Factor by Antithrombin III and Tissue Factor Pathway Inhibitor" *Blood* 82:1679–1680 (1993).

Broze, Jr. et al., "Regulation of Coagulation by a Multivalent Kunitz–Type Inhibitor" *Biochemistry* 29(33):7538–7546 (1990).

Broze, Jr., George J., "The Role of Tissue Factor Pathway Inhibitor in a Revised Coagulation Cascade" *Sem. in Hematology* 29(3):159–169 (1992).

Carson et al., "The role of tissue factor in the production of thrombin" *Blood. Coag. Fibrinol* 4:281–292 (1993).

Castro et al., "Does the Kunitz domain from the Alzheimer's amyloid Beta protein precursor inhibit a kallikrein responsible for post–translational processing of nerve growth factor precursor?" *FEBS* 267(2):207–212 (1990).

Chabbat et al., "Aprotinin Is A Competitive Inhibitor Of The Factor VIIa–Tissue Factor Complex" *Thrombosis Research* 71:205–215 (1993).

Chu et al., "Mosaic structure of globular domains in the human type VI collagen α 3 chain: similarity to von Willebrand Factor, fibronectin, actin, salivary proteins and aprotinin type protease inhibitors" *EMBO Journal* 9(2):385–393 (1990).

Creasey et al., "Tissue Factor Pathway Inhibitor Reduces Mortality from *Escherichia coli* Septic Shock" *J. Clin. Invest.* 91:2850–2860 (1993).

Creighton et al., "Biosynthesis, Processing, and Evolution of Bovine Pancreatic Trypsin Inhibitor" *Cold Spring Harbor Symp Quant Biol.* 52:511–519 (1987).

Cronlund et al., "A Low Molecular Weight Platelet Inhibitor of Factor XIa: Purification, Characterization, and Possible Role in Blood Coagulation" *Biochemistry* 31:1685–1694 (1992).

Davie et al., "The Coagulation Cascade: Initiation, Maintenance, and Regulation" *Biochemistry* 30(43):10363–10370 (1991).

De Maeyer et al. *Thrombosis & Haemostasis Abstracts XIV Congress of the Int'l Soc. on Thrombosis & Haemostasis* Ab 1245:888 (1993).

Fritz et al., "Biochemistry and Applications of Aprotinin, the Kallikrein Inhibitor from Bovine Organs" *Arzneimittel–Forschung/Drug Research* 33:479–494 (1983).

Fuhrer et al., "Aprotinin in cardiopulmonary bypass—effects on the Hageman factor (FXII)–Kallikrein system and blood loss" *Bllod Coagulation and Fibroanalysis* 3:99–104 (1992).

Girard et al., "Functional significance of the Kunitz–type inhibitor domains of lipoprotein–associated coagulation inhibitor" *Nature* 338:518–520 (1989).

Girard et al., "Inhibition of Factor VIIa–Tissue Factor Coagulation Activity by a Hybrid Protein" *Science* 248:1421–1424 (1990).

Hamamoto et al., "Inhibitory Properties of Full–length and Truncated Recombinant Tissue Factor Pathway Inhibitor TFPI" *Journal of Biological Chemistry* 268(12):8704–8710 (1993).

Haskel et al., "Prevention of Arterial Reocclusion After Thrombolysis With Recombinant Lipoprotein–Associated Coagulation Inhibitor" *Circulation* 84:821–827 (1991).

(List continued on next page.)

*Primary Examiner*—Dian C. Jacobson
*Attorney, Agent, or Firm*—Jeffrey S. Kubinec

[57] ABSTRACT

A potent serine protease inhibitor capable of inhibiting Factor VIIa, Factor XIa, plasma kallikrein, or plasmin is provided. The inhibitor is provided in a pharmaceutical composition for treatment of diseases where inhibition of Factor VIIa, Factor XIa, plasma kallikrein, or plasmin is indicated.

11 Claims, 7 Drawing Sheets

OTHER PUBLICATIONS

Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

Hynes et al., "X–ray Crystal Structure of the Protease Inhibitor Domain of Alzheimer's Amyloid Beta–Protein Precursor" *Biochemistry* 29:10018–10022 (1990).

Katori et al., "Evidence for the involvement of a plasma kallikrein–kinin system in the immediate hypotension produced by endotoxin in anaesthetized rats" *Br J Pharmacol* 98:1383–1391 (1989).

Kitchens et al., "Factor XI: A Review of Its Biochemistry and Deficiency" *Semi. in Thrombosis and Hemostasis* 17(1):55–72 (1991).

Kossiakoff et al., "Molecular recognition in biological systems: From activation to inhibition" *Bio. Society Transactions* 21:614–618 (1993).

Laskowski et al., "Protein Inhibitors of Proteinases" *Annu. Rev. Biochem.* 49:593–626 (1980).

Lawson et al., "Complex–dependent Inhibition of Factor VIIa by Antithrombin III and Heparin" *Journal of Biological Chemistry* 268(2):767–770 (1993).

Mann, Kenneth G., "Correspondence—Response" *Blood* 82:1680–1681 (1993).

Marks et al., "Mutants of Bovine Pancreatic Trypsin Inhibitor Lacking Cysteines 14 and 38 Can Fold Properly" *Science* 235:1370–1373 (1987).

McGrath et al., "The Sequence and Reactive Site of Ecotin" *Journal of Biological Chemistry* 266(10):6620–6625 (1991).

Nordfang et al., "The C–Terminus of Tissue Factor Pathway Inhibitor Is Essential to Its Anticoagulant Activity" *Biochemistry* 30:10371–10376 (1991).

Patston et al., "Reactivity of α 1–Antitrypsin Mutants against Proteolytic Enzymes of the Kallikrein–Kinin, Complement, and Fibrinolytic Systems" *Journal of Biological Chemistry* 265(18):10786–10791 (1990).

Petersen et al., "Characterization of Human Tissue Factor Pathway Inhibitor Variants Expressed in *Saccharomyces cerevisiae*" *Journal of Biological Chemistry* 268, N:13344–13351 (1993).

Rao et al., "Binding of Factor VIIa to Tissue Factor Permits Rapid Antithrombin III/Heparin Inhibition of Factor VIIa" *Blood* 81(10):2600–2607 (1993).

Roberts et al., "Directed evolution of a protein: Selection of potent neutrophil elastase inhibitors displayed on M13 fusion phage" *Proc. Natl. Acad. Sci USA* 89:2429–2433 (1992).

Royston, David, "The serine antiprotease aprotinin (Trasylol tm): a novel approach to reducing postoperative bleeding" *Blood Coag. Fibrinol* 1:55–69 (1990).

Salvesen et al., "Proteinase Inhibitors: /141–Macroglobulins, Serpins, and Kunins" *Hemostasis and Thrombosis: Basic Principles and Clin. Practice*, Colman et al., 3rd edition pps. 241–259 (1994).

Schapira et al., "Protection by Recombinant α 1–Antitrypsin Ala 357 Arg 358 against Arterial Hypotension Induced by Factor XII Fragment" *J. Clin. Invest.* 80:582–585 (1987).

Schmaier et al., "Protease Nexin–2/Amyloid Beta protein Precursor" *J. Clin. Invest.* 92:2540–2545 (1993).

Scott et al., "Alpha–1–antitrypsin–Pittsburgh: A Potent Inhibitor of Human Plasma Factor XIa, Kallikrein, and Factor XIIf" *J. Clin. Invest.* 77:631–634 (1986).

Scott et al., "Inactivation of Factor XIa by Plasma Protease Inhibitors" *J. Clin. Invest.* 69:844–852 (1982).

Scott et al., "Kinetics of Inhibition of Human Plasma Kallikrein by a Site–Specific Modified Inhibitor Arg 15—Aprotinin: Evaluation Using a Microplate System and Comparison With Other Proteases" *Blood* 69(5):1431–1436 (1987).

Sinha et al., "Conversion of the Alzheimer's Beta–Amyloid Precursor Protein (APP) Kunitz Domain into a Potent Human Neutrophil Elastase Inhibitor" *Journal of Biological Chemistry* 266(31):21011–21013 (1991).

Smith et al., "Platelet Coagulation Factor XIa–Inhibitor, a Form of Alzheimer Amyloid Precursor Protein" *Science* 248:1126–1128 (1990).

Thiele et al., "Gene Synthesis, Expression and Isolation of an Inhibitorily Active MS–2 pol–Stefin B Fusion Protein and Preparation of Des [Metl, 2/2] stefin B" *Biol. Chem. Hoppe–Seyler* 369:1167–1178 (1988).

Van Den Besselaar et al., "Tissue Factor–Induced Coagulation Can be Inhibited by Aprotinin (Trasylol)" *Thrombosis and Haemostasis* 69:298–299 (1993).

Van Nostrand et al., "Immunopurification and Protease Inhibitory Properties of Protease Nexin–2/Amyloid Beta–Protein Precursor" *Journal of Biological Chemistry* 265(17):9591–9594 (1990).

Vetr et al., "The domain structure of the inhibitor subunit of human inter–α–trypsin inhibitor reflects the exon structure of its gene" *FEBS 06902 Letter* 245(1,2):137–140 (1989).

Wachtfogel et al., "Aprotinin inhibits the contact, neutrophil, and platelet activation systems during simulated extracorporeal perfusion" *J. Thoracic and Cardiovascular Surgery* 106(1):1–10 (1993).

Wagner et al., "High Level Expression, Purification, and Characterization of the Kunitz–Type Protease Inhibitor Domain of Protease Nexin–2/Amyloid Beta–Protein Precursor" *Biochem. & Biophys. Res. Comm.* 186:1138–1145 (1992).

Dennis et al., "Kunitz Domain Inhibitors of Tissue Factor–Factor VIIa; I. Potent Inhibitors Selected from Libraries by Phage Display" *Journal of Biological Chemistry* 259(35):22129–22136 (1994).

Dennis et al., "Kunitz Domain Inhibitors of Tissue Factor–Factor VIIa; I. Potent and Specific Inhibitors by Competitive Phage Selection" *Journal of Biological Chemistry* 269(35):22137–22144 (1994).

Kido et al., "Protease–Specificity of Kunitz Inhibitor Domain of Alzheimer's Disease Amyloid Protein Precursor" *Biochem. & Biophys. Res. Comm.* 167(2):716–721 (1990).

Perona et al., "Crystal Structures of Rat Anioic Trypsin Complexed with the Protein Inhibitors APPI and BPTI" *J. Mol. Biol.* 230:919–933 (1993).

FIG. 2

|          | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|----------|---|---|---|---|---|---|---|---|---|----|----|----|----|----|----|----|----|----|----|----|----|----|----|----|----|----|----|----|----|
| TFPI-C   | V | R | E | V | C | S | E | Q | A | E  | P  | G  | P  | C  | R  | A  | L  | I  | L  | R  | W  | Y  | F  | D  | V  | T  | E  | G  | K  |
| APPI     | V | R | E | V | C | S | E | Q | A | E  | T  | G  | P  | C  | R  | A  | M  | I  | S  | R  | W  | Y  | F  | D  | V  | T  | E  | G  | K  |
| TFPI-KD1 | M | H | S | F | C | A | F | K | A | D  | D  | G  | P  | C  | K  | A  | I  | M  | K  | R  | F  | F  | F  | N  | I  | F  | T  | R  | Q  |
| TFPI-KD2 | K | P | D | F | C | F | L | E | E | D  | P  | G  | I  | C  | R  | G  | Y  | I  | T  | R  | Y  | F  | Y  | N  | N  | Q  | T  | K  | Q  |
| TFPI-KD3 | G | P | S | W | C | L | T | P | A | D  | R  | G  | L  | C  | R  | A  | N  | E  | N  | R  | F  | Y  | Y  | N  | S  | V  | I  | G  | K  |
| ITI-KD1  | K | E | D | S | C | Q | L | G | Y | S  | A  | G  | P  | C  | M  | G  | M  | T  | S  | R  | Y  | F  | Y  | N  | G  | T  | S  | M  | A  |
| ITI-KD2  | T | V | A | A | C | N | L | P | I | V  | R  | G  | P  | C  | R  | A  | F  | I  | Q  | L  | W  | A  | F  | D  | A  | V  | K  | G  | K  |
| Collagen α 3(VI) | E | T | D | I | C | K | L | P | K | D  | E  | G  | T  | C  | R  | D  | F  | I  | L  | K  | W  | Y  | Y  | D  | P  | N  | T  | K  | S  |
| HKIB9    | L | P | N | V | C | A | F | P | M | E  | K  | G  | P  | C  | Q  | T  | Y  | M  | T  | R  | W  | F  | F  | D  | N  | F  | E  | T  | G  |
| BPTI     | R | P | D | F | C | L | E | P | P | Y  | T  | G  | P  | C  | K  | A  | R  | I  | I  | R  | Y  | F  | Y  | N  | A  | K  | A  | G  | L  |
| MOTIF    | · | · | · | · | C | · | · | · | · | ·  | ·  | ·  | ·  | C  | ·  | ·  | ·  | ·  | ·  | ·  | ·  | ·  | ·  | ·  | ·  | ·  | ·  | ·  | ·  |

|          | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
|----------|----|----|----|----|----|----|----|----|----|----|----|----|----|----|----|----|----|----|----|----|----|----|----|----|----|----|----|----|----|
| TFPI-C   | C  | A  | P  | F  | F  | F  | G  | G  | C  | Y  | G  | N  | R  | N  | N  | F  | D  | T  | E  | E  | Y  | C  | A  | A  | V  | C  | C  | S  | A  |
| APPI     | C  | A  | P  | F  | F  | F  | G  | G  | C  | G  | G  | N  | R  | N  | N  | F  | D  | T  | E  | E  | Y  | C  | M  | A  | V  | C  | G  | S  | A  |
| TFPI-KD1 | C  | E  | E  | F  | I  | Y  | G  | G  | C  | E  | G  | N  | Q  | N  | R  | F  | E  | S  | L  | E  | E  | C  | K  | K  | M  | C  | T  | R  | D  |
| TFPI-KD2 | C  | E  | R  | F  | K  | Y  | G  | G  | C  | L  | G  | N  | M  | N  | N  | F  | E  | T  | L  | E  | E  | C  | K  | N  | I  | C  | E  | D  | G  |
| TFPI-KD3 | C  | E  | T  | F  | Q  | Y  | G  | G  | C  | G  | G  | N  | E  | N  | N  | F  | V  | S  | K  | Q  | E  | C  | L  | R  | A  | C  | K  | T  | V  |
| ITI-KD1  | C  | V  | L  | F  | P  | Y  | S  | G  | C  | M  | G  | N  | G  | N  | N  | F  | Y  | E  | E  | K  | E  | C  | L  | Q  | T  | C  | R  | G  | A  |
| ITI-KD2  | C  | A  | R  | F  | W  | Y  | G  | G  | C  | Q  | G  | N  | E  | N  | K  | F  | G  | S  | Q  | K  | E  | C  | R  | E  | Y  | C  | G  | V  | P  |
| Collagen α 3(VI) | C  | E  | L  | F  | A  | Y  | G  | G  | C  | G  | G  | N  | N  | N  | K  | F  | L  | R  | K  | E  | K  | E  | W  | K  | V  | K  | C  | A  | P  |
| HKIB9    | C  | Q  | T  | F  | V  | Y  | G  | G  | C  | R  | A  | K  | R  | N  | N  | F  | K  | S  | A  | E  | D  | C  | M  | R  | T  | C  | G  | G  | A  |
| BPTI     | C  | ·  | ·  | F  | ·  | Y  | ·  | G  | C  | ·  | ·  | ·  | ·  | N  | ·  | F  | ·  | ·  | ·  | ·  | ·  | C  | ·  | ·  | ·  | C  | ·  | ·  | ·  |
| MOTIF    | C  | ·  | ·  | F  | ·  | Y  | ·  | G  | C  | ·  | ·  | ·  | ·  | N  | ·  | F  | ·  | ·  | ·  | ·  | ·  | C  | ·  | ·  | ·  | C  | ·  | ·  | ·  |

| Inhibitor | 11 | 12 | 13 | 14 | 15 | 16 | 17 | 18 | 19 | 34 | 38 | 39 | TF·FVIIa Ki* (nM) | FXIa Ki* (nM) | Kallikrein Ki* (nM) | Plasmin Ki* (nM) |
|---|---|---|---|---|---|---|---|---|---|---|---|---|---|---|---|---|
| I-18 | P | G | V | C | R | A | L | – | L | F | C | G | 21 ± 5 | | | |
| I-49 | P | G | W | C | R | A | L | – | L | F | C | G | 13 ± 2 | | | |
| I-14 | P | G | F | C | R | A | L | – | L | F | C | G | 19 ± 2 | | | |
| I-16 | G | G | W | C | R | A | M | – | S | F | C | G | 35 ± 16 | | | |
| II-4 | P | G | P | C | R | A | M | – | S | F | C | Y | 42 ± 26 | | | |
| II-3 | P | G | W | C | R | A | M | – | S | – | C | G | 64 ± 12 | | | |
| II-6 | P | G | P | C | K | A | L | – | S | – | C | W | 374 ± 240 | | | |
| III-27 | T | G | P | C | R | A | L | – | L | W | C | G | 269 ± 74 | | | |
| III-30 | T | G | P | C | R | A | L | – | L | Y | C | G | 579 ± 385 | | | |
| TF7I-VY | P | G | V | C | R | A | L | – | L | F | C | Y | 2 | | | |
| TF7I-LY | P | G | L | C | R | A | L | – | L | F | C | Y | 3.1 ± 1.5 | | | |
| TF7I-WY | P | G | W | C | R | A | L | – | L | F | C | Y | 3.3 ± 1 | | | |
| TF7I-PG | P | G | P | C | R | A | L | – | L | F | C | G | 82 ± 10 | | | |
| I-18 | P | G | V | C | R | A | L | – | L | F | C | G | 21 ± 5 | | | |
| I-14 | P | G | F | C | R | A | L | – | L | F | C | G | 19 ± 2 | | | |
| I-49 | P | G | W | C | R | A | L | – | L | F | C | G | 13 ± 2 | | | |

FIG. 4A

| | | | | | | | | | | | | | | | | |
|---|---|---|---|---|---|---|---|---|---|---|---|---|---|---|---|---|
| IV-47C | P | G | P | C | R | A | M | M | K | I | C | H | 8.4 | 3175 | | 183 |
| IV-54C | P | G | P | C | R | A | L | M | K | V | C | Y | 2.7 ± 0.9 | 498 ± 264 | 476 | 126 ± 18 |
| IV-31B | P | G | P | C | R | A | L | M | K | V | C | F | 3.8 | 1927 | 81 ± 12 | 115 |
| IV-49C | P | G | P | C | R | A | M | M | K | I | C | Y | 2.8 | 2847 | 51.9 | 214 |
| IV-50C | P | G | P | C | R | A | M | Y | K | I | C | Y | 5.7 | 5094 | 277 | 144 |
| IV-57C | P | G | P | C | R | A | M | M | K | I | C | G | 9.6 | 370 | 1029 | 170 |
| | | | | | | | | | | | | | | | 212 | |
| IV-51C | P | G | P | C | K | A | L | M | R | Y | C | Y | 7.7 ± 0.6 | 1582 ± 643 | 2484 ± 292 | 1.7 ± 0.6 |
| IV-35B | P | G | P | C | K | A | — | M | K | I | C | H | 66 | 10610 | 10806 | 40 |
| IV-58C | P | G | P | C | K | A | L | M | K | Y | C | H | 19 | 9322 | 4408 | 4 |
| IV-48C | P | G | P | C | K | A | L | — | K | W | C | W | 13 | 6555 | 970 | 5.6 |
| IV-46C | P | G | P | C | K | A | M | M | K | L | C | Y | 33 | 7648 | 16345 | 146 |
| IV-55C | P | G | P | C | K | A | L | M | R | F | C | Y | 6.9 | 4820 | 3798 | 3.6 |
| IV-32B | P | G | P | C | K | A | L | Y | K | Y | C | Y | 7.9 ± 2.3 | 3784 ± 411 | 4697 ± 1051 | 3.7 ± 0.9 |
| IV-36B | P | G | P | C | K | A | L | M | K | V | C | G | 20 | 9008 | 7730 | 6.8 |
| IV-40B | P | G | P | A | K | A | M | Y | — | I | A | Y | 521 | 14862 | 17237 | 148 |
| 53b | P | G | P | C | R | A | L | I | L | F | A | Y | 3.3 ± 1.4 | 65 ± 16 | 89 ± 38 | 82 ± 38 |
| APPI | T | G | P | C | R | A | M | I | S | F | C | G | 301 ± 44 | 2.7 ± 1.4 | 515 ± 85 | 223 |
| TF71-C | P | G | P | C | R | A | L | L | L | F | C | Y | 1.9 ± 0.4 | 0.8 ± 0.5 | 1.2 ± 0.3 | 40 ± 6 |

FIG. 4B

FACTOR VIIA INHIBITORS FROM KUNITZ DOMAIN PROTEINS

FACTOR VIIa INHIBITORS FROM KUNITZ DOMAIN PROTEINS

This application is a continuation-in-part of co-pending U.S. application Ser. No. 08/206,310 filed 4 Mar. 1994.

FIELD OF THE INVENTION

This invention relates to novel Kunitz domain proteins having tissue factor-Factor VIIa inhibiting activity, DNA encoding these proteins, and recombinant materials and methods for producing these Factor VIIa inhibitors. The invention further relates to pharmaceutical compositions containing Factor VIIa inhibitors for treatment of diseases where inhibition of Factor VIIa, Factor XIa, plasma kallikrein, and plasmin is indicated.

BACKGROUND OF THE INVENTION

Thrombosis accounts for about 40% of the deaths in the United States. Current treatments for thrombotic disorders involve the use of anticoagulant drugs (e.g., heparin, coumadin) that have non-specific mechanisms of action. These drugs can cause bleeding thus limiting their use. Anticoagulants that block early steps in the coagulation cascade, and are specific for either the intrinsic or extrinsic pathways (see FIG. 1), could have superior efficacy and safety profiles because thrombotic events are suppressed without inducing bleeding episodes.

Factor VIIa

The tissue factor-Factor VIIa complex (TF-FVIIa) is a primary initiator of blood coagulation (Carson, S. D. and Brozna, J. P., *Blood Coag. Fibrinol.* 4:281–292 [1993]; Davie, E. W. et al., *Biochemistry* 30:10363–10370 [1991]; Rapaport, S. I. and L. V. M. Rao, *Arterioscler. Thromb.* 12:1111–1121 [1992]) (see FIG. 1). Factor VIIa (FVIIa), a 50 kDa, vitamin K-dependent, plasma serine protease, is generated by proteolysis of a single peptide bond from its zymogen Factor VII (FVII), which is present at ca. 0.5 $\mu$g/ml in plasma. Tissue factor (TF) contains 263 residues and is an integral membrane cofactor that is expressed constitutively in cells separated from plasma by the vascular endothelium (Carson, S. D. and J. P. Brozna, *Blood Coag Fibrinol* 4:281–292 [1993]). Upon tissue injury, the exposed extracellular domain of TF can bind and activate FVII to form a high affinity TF-FVIIa complex. Factor XIIa (FXIIa) has also been implicated in the activation of FVII. The TF-FVIIa complex initiates the extrinsic pathway of the coagulation cascade by activation of Factor X (FX) to Factor Xa (FXa) , Factor IX (FIX) to Factor IXa (FIXa), and additional FVII to FVIIa. This leads to the conversion of prothrombin to thrombin, which carries out many biological functions (Badimon, L. et al., *Trends Cardiovasc. Med.* 1:261–267 [1991]). Among the most important functions of thrombin is the conversion of fibrinogen to fibrin, which polymerizes to form a clot.

The regulation of coagulation is critical to maintaining hemostasis. Following initiation of the coagulation cascade, TF-FVIIa is regulated by tissue factor pathway inhibitor (TFPI), a feedback inhibitor that prevents further activation of zymogen substrates (Broze Jr., G. J. et al., *Biochemistry* 29:7539–7546 [1990]; Broze Jr., G. J., *Semin. Hematol.* 29:159–169 [1992]). TFPI is also known as LACI or EPI for lipoprotein associated coagulation inhibitor and extrinsic pathway inhibitor, respectively. TFPI contains an acidic amino terminal region followed by three Kunitz-type domains and a basic carboxy terminal region. TFPI is thought to inhibit TF-FVIIa in a FXa dependent manner, first binding FXa via the second Kunitz domain followed by binding FVIIa via the first Kunitz domain (Girard, T. J. et al., *Nature* 338:518–520 [1989]). In the absence of FXa, TFPI is a poor inhibitor of the TF-FVIIa complex (Girard, T. J. et al., *Science 248:1421–1424* [*1990*]). Recently, the serpin antithrombin III (AT III) has also been shown to inhibit TF-FVIIa activity in the presence of heparin (Rao, L. V. M. et al., *Blood* 81:2600–2607 [1993]; Lawson, J. H. et al., *J. Biol. Chem.* 268:767–770 [1993]; Broze Jr., G. J. et al., *Blood* 82:1679–1680 [1993]; Mann, K. G., *Blood* 82:1680–1681 [1993]). Inhibition of TF-FVIIa by TFPI is reversible, whereas inhibition by ATIII is essentially irreversible. The relative importance of ATIII/heparin inhibition of TF-FVIIa versus TFPI is unknown in vivo.

Variants of TFPI have been made that also inhibit TF-FVIIa activity. In particular a variant that contains the first two Kunitz domains (residues 1–161) has been made and characterized (Hamamoto et al. *J. Biol. Chem.* 268:8704–8710 [1993]; Petersen et al. *J. Biol. Chem.* 268:13344–13351 [1993]). TFPI and variants have been shown to affect hemostasis in animal models of arterial reocclusion after thrombolysis (Haskel, E. J. et al., *Circulation* 84:821–827 [1991]), venous thrombosis (Holst, J. et al., *Haemostasis* 23 (suppl 1):112–117 [1993]), and disseminated intravascular coagulation resulting from septic shock (Creasey, A. A. et al., *J. Clin. Invest.* 91:2850–2860 [1993]). However, TFPI may not have all of the properties desired for an anticoagulant agent for the treatment of thrombotic disease. The dependence of FXa inhibition by TFPI prior to the inhibition of TF-FVIIa may have undesirable effects. For instance, since FXa is produced by both the intrinsic and extrinsic pathways, inhibition of FXa may totally inhibit coagulation and lead to undesirable side effects such as bleeding; a selective inhibitor of the extrinsic or intrinsic pathways may not lead to this problem. In addition heparin may affect the activity of TFPI. The carboxyl terminus of TFPI may be required for maximal activity (Wesselschmidt, R. et al., *Blood* 79:2004–2010 [1992]; Nordfang, O. et al., *Biochemistry* 30:10371–10376 [1991]) Furthermore, TFPI is cleaved by human leukocyte elastase between the first two Kunitz domains which results in the loss of TF-FVIIa inhibitory activity (Higuchi, D. A. et al., *Blood* 79:1712–1719 [1992]).

Bovine pancreatic trypsin inhibitor (BPTI), also referred to as aprotinin, has recently been shown to competitively inhibit TF-FVIIa activity, albeit with relatively weak affinity (Ki=30 $\mu$M) (Chabbat, J. et al., *Thromb Res* 71:205–215 [1993]). In addition, BPTI has recently been shown to inhibit TF-induced coagulation; however, ca. 75 pM was needed to prolong the clotting time 1.4-fold in a PT assay (van den Besselaar, A. M. H. P. et al., *Thromb Haemostas* 69:298–299 [1993]).

Factor XIa

Factor XIa (FXIa) is a glycosylated serine protease produced in blood from its zymogen, Factor XI (FXI). It is composed of a homodimer of two identical disulfide-linked proteins each having a molecular weight of 80,000 Da (Kitchens, C. S., *Semin. Thromb. Hemostas.* 17:55–72 [1991]). In blood, most of the protein circulates bound to high molecular weight kininogen (HMWK). FXI is normally present at a concentration of ca. 4.5 $\mu$g/ml. It can be activated by a number of serine proteases; FXIIa is thought to be a major activator, although thrombin has also recently been implicated (Galiani, D. and Broze Jr., G. J., *Science* 253:909–912 [1991]). In the presence of high molecular weight kininogen, FXIIa can activate prekallikrein to kallikrein and FXI to FXIa; the kallikrein formed can activate more Factor XII to FXIIa. FXIa activates FIX to FIXa, which in the presence of Factor VIII leads to the formation of FXa and ultimately a fibrin clot (see FIG. 1).

The major physiological inhibitor of FXIa is thought to be the serpin α1-antitrypsin, also known as α1-proteinase inhibitor (Scott, C. F. et al., *J. Clin. Invest.* 69:844–852 [1982]). Serpins (serine protease inhibitors) such as $\alpha_1$-proteinase inhibitor have been well characterized for their ability to inhibit various proteases because of their therapeutic potential to control proteolysis in thrombosis, shock, and inflammation (Schapira, M. et al., *Trends Cardiovasc. Med.,* 4:146–151[1991]; Patston, P. A. et al.,*J. Biol. Chem.* 265:10786–10791 [1990]) and because spontaneous mutations to the $P_1$ residue (M358R; $\alpha_1$-proteinase inhibitor-Pittsburgh) dramatically alter the protease inhibitor specificity (Scott, C. F. et al., *J. Clin. Invest.* 77:631–634 [1986]). However other serpins may inhibit FXIa; these include C1 inhibitor, α2-antiplasmin, and antithrombin-III. α2-macroglobulin is another inhibitor of FXIa. A low molecular weight inhibitor termed PIXI has also been characterized from platelets (Cronlund, A. L. and Walsh, P. N., *Biochemistry* 31:1685–1694 [1992]).

Another inhibitor of FXIa is protease nexin-2, the secreted form of the Alzheimer's amyloid β-protein precursor, sometimes referred to as $A\beta PP_{751}$ and $A\beta PP_{770}$ for the different isoforms of this protein (Van Nostrand, W. E. et al., *J. Biol. Chem.* 265:9591–9594 [1990]; Wagner, S. L. et al., *Biochem. Biophys. Res. Commun.* 186:1138–1145 [1992]; Smith, R. P. et al, *Science* 248:1126–1128 [1990]). This protein contains a Kunitz domain which has been designated KPI (61 residues) (Wagner, S. L. et al., *Biochem. Biophys. Res. Commun.* 186:1138–1145 [1992]) or APPI (58 residues) (Hynes, T. R. et al., *Biochemistry* 29:10018–10022 [1990]). The KPI domain itself is also a potent inhibitor of FXIa (Wagner, S. L. et al., *Biochem. Biophys. Res. Commun.* 186:1138–1145 [1992]). Heparin has been shown to potentiate the inhibition of FXIa by protease nexin-2, but not by the KPI domain itself (Wagner, S. L. et al., *Biochem. Biophys. Res. Commun.* 186:1138–1145 [1992]). A variant of BPTI having arginine at position 15 has been made semisynthetically and found to inhibit FXIa with relatively high affinity (Scott, C. F. et al., *Blood* 69:1431–1436 [1987]).

Kallikrein

Prekallikrein is a glycoprotein comprised of a single polypeptide chain with a molecular weight of 80,000 Da and is present in normal plasma at a concentration of ca. 50 μg/ml (600 nM). In blood, 75% of prekallikrein circulates bound to HMWK. It is a serine protease zymogen which can be activated by FXIIa (see FIG. 1). Kallikrein consists of 2 disulfide bonded chains of 43,000 and 33,000–36,000 Da. The light chain of kallikrein contains the enzymatic domain while the heavy chain appears to be required for surface dependent activation of coagulation.

Kallikrein cleaves HMWK to form bradykinin (a potent vasodilator and endothelial cell activator), can activate prourokinase and plasminogen (fibrinolytic), and feeds back for reciprocal activation of surface bound FXII to FXIIa (see FIG. 1). In addition it can also stimulate neutrophils causing the release of elastase. Both Factor XIIa and kallikrein can lead to plasmin generation causing fibrinolysis.

The major physiological inhibitor of kallikrein is the serpin C1 inhibitor, which inhibits irreversibly. In a purified system HMWK has been shown to protect kallikrein from inhibition by C1 inhibitor although both proteins bind to kallikrein at different sites. α2-macroglobulin is another major inhibitor of kallikrein. Antithrombin-III can also inhibit kallikrein, but slowly even in the presence of heparin. α2-antiplasmin and α1-antitrypsin are poor inhibitors of kallikrein. A mutant form of $\alpha_1$-proteinase inhibitor ($\alpha_1$-proteinase inhibitor-Pittsburgh) that contains an Arg in the $P_1$ position and an Ala in the $P_2$ position has been shown to be a more potent inhibitor of Factor XIIf (FXIIf) and kallikrein compared to C1 inhibitor, the most potent known natural inhibitor of these proteases (Schapira, M. et al., *J. Clin. Invest* 80:582–585 [1987]; Patston, P. A. et al., *J. Biol. Chem.* 265:10786–10791 [1990]). Rats treated with this mutant were partially protected from the hypotension resulting from injection of FXIIf.

Basic pancreatic trypsin inhibitor (BPTI, aprotinin) reversibly inhibits plasma kallikrein as well as plasmin and a number of other serine proteases; the $P_1$ residue of BPTI is a Lys. A variant of BPTI having arginine at position 15 has been made semisynthetically and found to inhibit plasma kallikrein with a Ki of 15 nM, about 20-fold higher affinity than BPTI (Scott, C. F. et al., *Blood* 69:1431–1436 [1987]). BPTI has been used to treat patients with acute pancreatitis (Fritz, H. and Wunderer, G., *Arzneim.-Forsch. Drug Res.* 33:479–494 [1983]). The use of aprotinin and the possible involvement of the contact pathway (see below) has also been described for the reduction of bleeding from postoperative surgery (Royston, D. *Blood Coag. Fibrinol.* 1:55–69 [1990]) and in cardiopulmonary bypass surgery and for use in extracorporeal circulation models (Fuhrer, G. et al., *Blood Coag. Fibrinol.* 3:99–104 [1992]; Wachtfogel, Y. T. et al., *J. Thorac. Cardiavasc. Surg.* 106:1–10 [1993]). Similarly, soybean trypsin inhibitor has been shown to inhibit bradykinin formation and the initial hypotension induced by endotoxin in rats (Katori, M. et al., *Br. J. Pharmacol.* 98:1383–1391 [1989]).

TF-FVIIa in Disease (Thrombosis)

The formation of the TF-FVIIa complex is thought to be the key event initiating the coagulation cascade (Carson, S. D. and J. P. Brozna, *Blood Coag Fibrinol* 4:281–292 [1993; Davie, E. W. et al., *Biochemistry* 30:10363–10370 [1991; Rapaport, S. I. and L. V. M. Rao, *Arterioscler. Thromb.* 12:1111–1121 [1992]). TF is found on the surface of the endothelium as well as monocytes and may become activated during the inflammatory response (Altieri, D. A., *Blood* 81:569–579 [1993]). Thus, inhibitors of the TF-FVIIa complex may be useful as anticoagulants and as antiinflammatory agents. A monoclonal antibody to TF has been shown to prevent mortality in a baboon model of septic shock (Taylor Jr., F. B. et al., *Circ. Shock 33:127–134 [1991]*). A TF antibody has also shown that TF may play a role in focal cerebral ischemia (Thomas, W. S. et al., *Stroke* 24:847–854 [1993]). In a rabbit model of thrombosis, a monoclonal antibody against rabbit TF inhibited thrombus formation in carotid arteries (Pawashe, A. B. et al., *Circ. Res.* 74:56–63 [1994]).

Contact Activation Pathways in Disease

Contact activation is a surface mediated pathway responsible in part for the regulation of inflammation and thrombosis as mediated by coagulation, kinin, fibrinolysis, complement, and other relevant pathways (see FIG. 1). The proteins involved in this pathway include FXII (Hageman Factor), prekallikrein (Fletcher Factor), FXI, high molecular weight kininogen (HMWK), and C1 inhibitor (DeLa Cadena, R. A., et al. in *Hemostasis and Thrombosis: Basic Principles and Clinical Practice* (Colman, R. W., Hirsh, J., Marder, V., & Salzman, E. W., eds.) pp. 219–240, J. B. Lippincott Co., Philadelphia[1994]; Wachtfogel, Y. T. et al., *Thromb. Res.* 72:1–21 [1993]). The involvement of this plasma protease system has been suggested to play a significant role in a variety of clinical manifestations including septic shock, adult respiratory distress syndrome (ARDS), disseminated intravascular coagulation (DIC), cardiopulmonary bypass surgery, bleeding from postoperative surgery, and various other disease states (Colman, R. W., *N. Engl. J. Med* 320:1207–1209 [1989]; Bone, R. C., *Arch. Intern. Med.* 152:1381–1389 [1992]).

Septic Shock

Septic shock is the most common cause of death of humans in intensive care units in the United States (Parillo, J. E. et al., *Ann. Int. Med.* 113:227–242 [1990]; Schmeichel C. J. and McCormick D., *BioTechnol.* 10:264–267 [1992]). It is usually initiated by a local nidus of infection that invades the blood stream. Incidences of sepsis and shock can arise from infections with either gram negative, gram positive bacterial or fungal microorganisms. All these organisms seem to induce a common pattern of cardiovascular dysfunction. In recent years aggressive fluid infusion therapy has been accepted as a primary means of treatment for septic shock. Adequate repletion of fluid is associated with an elevated cardiac output and low vascular resistance. Despite treatment, septic shock results in a severe decrease in systemic vascular resistance and generalized blood flow maldistribution. Aggressive therapy reverses shock and death in about 50% of the cases. Unresponsive hypotension resulting from a very low vascular resistance cannot be corrected by fluid infusion. Among those subjects that die from septic shock, approximately 75% die from persistent hypotension and the remainder due to multiple organ system failure (see FIG. 1).

The increase in cardiac output and vasodilation in septic shock is attributed to the action of inflammatory mediators. While the actual events leading to septic shock, DIC and hypotension have not been established, the known interactions among various components of the many physiological systems suggest that activation of the contact pathway may lead to a state of septic shock, multiorgan failure, and death (Bone, R. C., *Arch. Intern. Med.* 152:1381–1389 [1992]) as illustrated in FIG. 1. The contact system of intrinsic coagulation and the complement system are excessively activated in sepsis and septic shock, especially in cases of fatal septic shock. The contact system can participate in the generation of many vasoactive mediators such as bradykinin, FXIIa, FXIIf and C5a, which are thought to play a role in the pathogenesis of fatal shock. Bradykinin, FXIIa, and FXIIf are potent inducers of hypotension while C5a is an inducer of vasodilation and vasopermeability. The levels of FXII, prekallikrein, and high molecular weight kininogen are decreased significantly during non-fatal shock, but are most severely depressed during fatal septic shock to approximately 30%, 57% and 27% of normal values respectively. These changes are noted regardless of whether the septic state is caused by gram positive or gram negative bacteria. The contact activation pathway is also involved in both fibrin deposition and lysis, as well as triggering neutrophil activation, activation of complement and modulation of blood pressure.

Decreased levels of prekallikrein are observed in hepatic disease, DIC, chronic renal failure and nephritic syndrome. In septic shock, components of the kallikrein-kinin system are depleted suggesting activation of this system. This is not the case in cardiogenic shock suggesting that the kallikrein-kinin system is a key player in septic shock (Martinez-Brotons F. et al., *Thromb. Haemostas.* 58:709–713 [1987])

ARDS

ARDS is a complex pulmonary disorder affecting 150,000 people in the U.S. yearly with a 50% mortality rate. Leukocytes, platelets and the proteolytic pathways of coagulation and complement mediate ARDS. ARDS involves activation of the contact activation pathway and depletion of C1 inhibitor. Sepsis induced ARDS results in more severe DIC and fibrinolysis, more fibrin degradation products and reduced ATIII levels compared to trauma induced ARDS (Carvalho, A. C. et al., *J. Lab. Clin. Med.* 112:270–277 [1988]).

Disseminated Intravascular Coagulation

Disseminated intravascular coagulation (DIC) is a disorder that occurs in response to tissue injury and invading microorganisms characterized by widespread deposition of fibrin and depleted levels of fibrinogen (Muller-Berghaus, G. *Semin. Thromb. Hemostasis* 15:58–87 [1989]). There are prolonged prothrombin and activated partial thromboplastin times. DIC has been observed in the clinical settings of a wide variety of diseases (Fruchtman, S. M. and Rand, J. H. in *Thrombosis in Cardiovascular Disorders* (Fuster, V. and Verstraete M., eds.) pp. 501–513 W. B. Saunders, Philadelphia [1992]).

Hypotension, DIC, and neutrophil activation are all triggered by the interaction of Factor XIIa, plasma kininogens and kallikrein. Deficiency of any of these 3 proteins does not give rise to hemostatic disorders due to redundancy in the system due to platelets, other coagulation factors, and endothelial cells.

A large number of therapeutic approaches to septic shock and related disorders have been identified including various cytokine antagonists, Mabs (to endotoxin, tissue factor, tumor necrosis factor (TNF), neutrophils, etc.), kinin antagonists, bactericidal permeability increasing protein, PAF antagonists, C1 inhibitor, DEGR-FXa, activated protein C, and many other approaches. It is possible, due to the complicated nature of the disease, that an approach that involves multiple agents or agents that effect multiple pathways may be successful in the treatment of septic shock (Schmeichel C. J. and McCormick D., *BioTechnol.* 10:264–267 [1992]).

Kunitz Domain Inhibitors of Serine Proteases

The Kunitz-type protease inhibitor domains found in TFPI are found among other mammalian proteins including BPTI, Alzheimer's amyloid β-protein precursor, and inter-α-trypsin inhibitor (Creighton, T. E. and I. G. Charles, *Cold Spring Harbor Symp. Quant. Biol.* 52:511–519 [1987]; Salvesen, G. and Pizzo, S., in *Hemostasis and Thrombosis: Basic Principles and Clinical Practice* (Colman, R. W., Hirsh, J., Marder, V., & Salzman, E. W., eds.) pp. 241–258, J. B. Lippincott Co., Philadelphia[1994]) (FIG. 2). Kunitz-type protease inhibitors have also been prepared from the α-3 chain of human type VI collagen (see WO 93/14119). They have also been identified in many snake venoms. Recently, Kunitz inhibitors of TF-FVIIa have been prepared from BPTI using phage display technology (De Maeyer et al., *Thrombosis and Haemostasis Abstracts,* XIVth Congress of the International Society on Thrombosis and Haemostasis, p 888 Ab. No. 1245 [1993]). These authors report a mutant BPTI (T11D, K15R, R17L, I18H, I19L, V34Y, R39L and K46E) having a $K_i$ for TF-FVIIa of 0.5 nM.

Kunitz domains are generally stable proteins containing about 60 residues and six specifically spaced cysteines that are present in disulfide bonds. They are known to be slow, tight-binding, reversible inhibitors of serine proteases that bind to the active site and inhibit according to the standard mechanism. Subsequent cleavage between the $P_1$ and $P_1'$ residues occurs very slowly if at all (Bode, W. and Huber, R., *Eur. J. Biochem.* 204:433–451 [1992]; Laskowski, M., Jr. and Kato, I., *Annu. Rev. Biochem.* 49:593–626 [1980]). There are many interactions between the serine protease subsites and the side chains in the primary binding loop of Kunitz domains ($P_5$–$P_4'$) (Bode, W. and Huber, R., *Eur. J. Biochem.* 204:433–451 [1992]; Laskowski, M., Jr. and Kato, I., *Annu. Rev. Biochem.* 49:593–626 [1980]); however, the interactions of the $P_1$ residue with the specificity pocket are energetically most important and therefore represent the primary specificity determinants (see FIG. 3). Substrates and inhibitors of TF-FVIIa and other trypsin-like proteases such as FXIa and kallikrein have either Arg or Lys at the $P_1$ residue. Therefore, at position 15 ($P_1$), either Arg or Lys is generally preferred. However methionine is sometimes found at the $P_1$ position and may also be preferable for good inhibition of serine proteases (McGrath, M. E. et al., *J. Biol. Chem.* 266:6620–6625 [1991]). The introduction of residues such as Val, Leu, or Ile at the $P_1$ position of Kunitz domains leads to potent inhibitors of human leukocyte elastase (HLE) and concomitant loss of the wild type inhibitory activity (Beckmann, J. et al., *Eur. J. Biochem.* 176:675–682 [1988]; Sinha, S. et al., *J. Biol. Chem.* 266:21011–21013 [1991]). Residues other than naturally occurring amino acids have also been substituted into Kunitz domains and other related protease inhibitor domains by chemical synthesis (Beckmann, J. et al., *Eur. J. Biochem.* 176:675–682 [1988]; Bigler, T. L. et al., *Prot. Sci.* 2:786–799 [1993]).

The crystal structures of Kunitz domains reveal key residues likely to make contact with the serine protease domain of FVIIa and other serine proteases (Hynes, T. R. et al., *Biochemistry* 29:10018–10022 [1990; Bode, W. and Huber, R., *Eur. J. Biochem.* 204:433–451 [1992]; Kossiakoff, A. A. et al., *Biochem Soc Trans* 21:614–618 [1993]). Although the amino acid at the $P_1$ position generally dominates the affinity of inhibitors for the serine protease active site (Scott, C. F. et al., *Blood* 69:1431–1436 [1987; Laskowski, M., Jr. and Kato, I., *Annu. Rev. Biochem.* 49:593–626 [1980]; Beckmann, J. et al., *Eur. J. Biochem.* 176:675–682 [1988]; Sinha, S. et al., *J. Biol. Chem.* 266:21011–21013 [1991]), residues outside this region are also known to play a role in binding affinity and specificity towards serine proteases (Kossiakoff, A. A. et al., *Biochem. Soc. Trans.* 21:614–618 [1993]; Roberts, B. L. et al., *Proc Natl Acad Sci U.S.A.* 89:2429–2433 [1992]). Some of the contact residues in the binding loop (positions 11, 15, 17, and 19) are relatively variable among Kunitz domains (Creighton, T. E. and I. G. Charles, *Cold Spring Harbor Symp. Quant. Biol.* 52:511–519 [1987]). Position 13 is normally a Pro; however, other residues are sometimes found here. Position 12 is almost always a Gly. In addition to recruiting any side chain interactions, substitution of other residues for Pro and vice versa might also lead to conformational changes in the main chain which could affect binding. The cysteine residues at positions 14 and 38 that form a disulfide bond are always found in Kunitz domains; however other residues such as Ala, Gly, Ser, or Thr may substitute for the cysteines (Marks, C. B. et al., *Science,* 235:1370–1373 [1987]).

In APPI and other Kunitz domains, residues 13 and 39 as well as residues 17 and 34 are in close proximity (FIG. 3) (Hynes, T. R. et al., *Biochemistry* 29:10018–10022 [1990]). Therefore, the potential interactions of residues 34 and 39 with the primary binding loop of APPI were investigated to address whether these positions would affect binding. Residues at positions 16 and 18 are generally more invariant among Kunitz domains (Creighton, T. E. and I. G. Charles, *Cold Spring Harbor Symp. Quant. Biol.* 52:511–519 [1987]); however, different residues at these positions may also alter binding. Therefore, residues at positions 11 through 19, 34, 38, and 39 may all affect the binding affinity and specificity towards serine proteases (FIG. 3). However, other residues are important as well. For instance, APPI and BPTI have a methionine at position 52, although other Kunitz domains have a variety of residues at this position (FIG. 2). Methionine at this position can be replaced by different residues which may be beneficial with respect to producing the protein. For example, methionine is susceptible to oxidation to form methionine sulfoxide, which can complicate purification. Also protein can be made recombinantly as a fusion protein, followed by cleavage with CNBr, which cleaves at methionine residues (Auerswald, E. A. et al., *Biol. Chem. Hoppe-Seyler* 369:27–35 [1988]). Therefore, it is necessary to remove other methionine residues in the protein of interest to produce intact product. Substitutions at position 52 are not expected to have major effects on inhibitory activity since it is so far away from the primary binding loop of the Kunitz domain (FIG. 3).

The 61 residue Kunitz protease inhibitor domain of the Alzheimer's amyloid β-protein precursor (KPI), binds to the active site of mammalian serine proteases trypsin, chymotrypsin and Factor XIa with high affinity (Wagner, S. L. et al., *Biochem. Biophys. Res. Commun.* 186:1138–1145 [1992]). Similar results were found with a fusion protein containing this domain (Sinha, S. et al., *J. Biol. Chem.* 266:21011–21013 [1991]). The KPI domain has also been shown to inhibit FIXa activity, although much less potently than protease nexin-2, from which it was derived (Schmaier A. H. et al., *J. Clin. Invest.* 92:2540–2545 [1993]). The KPI domain at 100 μM independently inhibited the coagulant activity of both Factor Xa and VIIa in plasma more than twofold over control. However, this inhibition was at least two orders of magnitude weaker than the inhibition of Factor XIa by the KPI domain, which at ~0.5 μM resulted in a twofold prolongation of the Factor XIa coagulant assay. We chose APPI as a scaffold since (a) it has been readily expressed in bacteria such as *E. coli* (Castro, M. et al., *FEBS Lett.* 267:207–212 [1990]) and yeast such as *P. pastoris,* (b) an x-ray crystal structure of the protein is known (Hynes, T. R. et al., *Biochemistry* 29:10018–10022 [1990]), and (c) it is derived from a human sequence, which would minimize the immunogenicity for any therapeutically useful variants. Other Kunitz domains from human and other mammalian sources may be used similarly.

Accordingly, it is an object of this invention to provide potent serine protease inhibitors that reversibly inhibit proteases of the coagulation, contact activation, fibrinolysis, inflammation, complement activation, and hypotensive pathways for the treatment of diseases that are affected by these pathways. It is further an object of this invention to provide potent inhibitors capable of inhibiting Factor VIIa, Factor XIa, kallikrein, and plasmin. Additionally, it is an object to provide synthetic methods for producing these inhibitors for therapeutic intervention. These and other objects will be apparent from consideration of this application as a whole.

SUMMARY OF THE INVENTION

By means of the present invention the objectives described above have been realized, and there is accordingly provided herein a composition of matter capable of inhibiting a serine protease selected from Factor VIIa, Factor XIa, plasma kallikrein, and plasmin, comprising a purified polypeptide having an amino acid sequence represented by Structural Formula I:

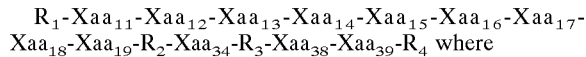

where $R_1$ represents a peptide comprising from 5 to 250 naturally occurring amino acid residues wherein at least one residue is Cys;

$R_2$ represents a peptide having 14 amino acid residues wherein at least one residue is Cys;

$R_3$ represents a tripeptide;

$R_4$ represents a peptide comprising from 12 to 250 amino acid residues wherein at least one residue is Cys;

$Xaa_{11}$ is a naturally occurring amino acid residue selected from the group Pro, Arg, Ala, Glu, Gly, and Thr;

$Xaa_{12}$ represents Gly;

$Xaa_{13}$ is a naturally occurring amino acid residue selected from the group Pro, Leu, Trp, Val, Gly, Phe, His, Tyr, Ala, Ile, Glu, and Gln;

$Xaa_{14}$ is a naturally occurring amino acid residue selected from Cys, Ala, Ser, Thr, and Gly;

$Xaa_{15}$ is a naturally occurring amino acid residue selected from Met, Arg, and Lys;

$Xaa_{16}$ is a naturally occurring amino acid residue selected from Gly and Ala;

$Xaa_{17}$ is a naturally occurring amino acid residue selected from the group Met, Leu, Ile, Arg, Tyr, and Ser;

$Xaa_{18}$ is a naturally occurring amino acid residue selected from the group Ile, His, Leu, Met, Tyr, and Phe;

$Xaa_{19}$ is a naturally occurring amino acid residue selected from the group Leu, Arg, Ala, Lys, and Ile;

$Xaa_{34}$ is a naturally occurring amino acid residue selected from the group Phe, Ile, Ser, Leu, Tyr, Trp, and Val;

$Xaa_{38}$ is a naturally occurring amino acid residue selected from Cys, Ala, Ser, Thr, and Gly; and $Xaa_{39}$ is a naturally occurring amino acid residue selected from the group Tyr, Gly, Trp, His, and Phe; provided $R_1$ is not $Xaa^1$-Asp-Ile-Cys-Lys-Leu-Pro-Lys-Asp (SEQ ID NO: 1), where Xaa is His or 1–5 amino acid residues; and $Xaa_{11}$ through $Xaa_{19}$ are not Pro-Gly-Phe-Ala-Lys-Ala-Ile-Ile-Arg (SEQ ID NO: 2);

Thr-Gly-Leu-Cys-Lys-Ala-Tyr-Ile-Arg (SEQ ID NO: 3);

Thr-Gly-Leu-Cys-Lys-Ala-Arg-Ile-Arg (SEQ ID NO: 4); and

Ala-Gly-Ala-Ala-Lys-Ala-Leu-Leu-Ala (SEQ ID NO: 5).

A preferred polypeptide represented by Formula I has an apparent dissociation constant ($K_i^*$) with respect to tissue factor-Factor VIIa of less than about 100 nM, more preferably less than 10 nM and most preferably 3 nM or lower. Optionally, the preferred polypeptide also has an apparent dissociation constant ($K_i^*$) with respect to both Factor XIa and kallikrein of less than about 10 nM and most preferably 2 nM or lower. Polypeptides of Formula I that are potent inhibitors of all three of; TF-FVIIa, FXIa, and kallikrein preferably have $Xaa_{18}$–$Xaa_{19}$ as Ile-Leu. Optionally, the preferred polypeptide specifically inhibits TF-FVIIa and has an apparent dissociation constant ($K_i^*$) with respect to both Factor XIa and kallikrein of greater than about 50 nM and most preferably greater than about 80 nM. Polypeptides of Formula I that are specific potent inhibitors of TF-FVIIa preferably have $Xaa_{18}$–$Xaa_{19}$ as Met-Lys/Arg.

The preferred polypeptide represented by Structural Formula I comprises about 58 amino acid residues in which $R_1$ is a 10 residue peptide, $R_2$ is a 14 residue peptide, $R_3$ is a tripeptide, and $R_4$ is a 19 residue peptide, and where residue 5, 14, 30, 38, 51 and 55 are Cys. Also preferably, residues 12 and 37 are G, residues 33 and 45 are Phe, residue 35 is Tyr and residue 43 is Asn.

Exemplary preferred polypeptides of Structural Formula I are as follows:

$R_1$ is selected from the group

Val-Arg-Glu-Val-Cys-Ser-Glu-Gln-Ala-Glu (SEQ ID NO: 6);

Met-His-Ser-Phe-Cys-Ala-Phe-Lys-Ala-Asp (SEQ ID NO: 7);

Lys-Pro-Asp-Phe-Cys-Phe-Leu-Glu-Glu-Asp (SEQ ID NO: 8);

Gly-Pro-Ser-Trp-Cys-Leu-Thr-Pro-Ala-Asp (SEQ ID NO: 9);

Lys-Glu-Asp-Ser-Cys-Gln-Leu-Gly-Tyr-Ser (SEQ ID NO: 10);

Thr-Val-Ala-Ala-Cys-Asn-Leu-Pro-Ile-Val (SEQ ID NO: 11);

Leu-Pro-Asn-Val-Cys-Ala-Phe-Pro-Met-Glu (SEQ ID NO: 12); and

Arg-Pro-Asp-Phe-Cys-Leu-Glu-Pro-Pro-Tyr (SEQ ID NO: 13);

$R_2$ is selected from the group

Arg-Trp-Tyr-Phe-Asp-Val-Thr-Glu-Gly-Lys-Cys-Ala-Pro-Phe (SEQ ID NO: 14);

Arg-Phe-Phe-Phe-Asn-Ile-Phe-Thr-Arg-Gln-Cys-Glu-Glu-Phe (SEQ ID NO: 15);

Arg-Tyr-Phe-Tyr-Asn-Asn-Gln-Thr-Lys-Gln-Cys-Glu-Arg-Phe (SEQ ID NO: 16);

Arg-Phe-Tyr-Tyr-Asn-Ser-Val-Ile-Gly-Lys-Cys-Arg-Pro-Phe (SEQ ID NO: 17);

Arg-Tyr-Phe-Tyr-Asn-Gly-Thr-Ser-Met-Ala-Cys-Glu-Thr-Phe (SEQ ID NO: 18);

Leu-Trp-Ala-Phe-Asp-Ala-Val-Lys-Gly-Lys-Cys-Val-Leu-Phe (SEQ ID NO: 19);

Lys-Trp-Tyr-Tyr-Asp-Pro-Asn-Thr-Lys-Ser-Cys-Ala-Arg-Phe (SEQ ID NO: 20;

Arg-Trp-Phe-Phe-Asn-Phe-Glu-Thr-Gly-Glu-Cys-Glu-Leu-Phe (SEQ ID NO: 21); and

Arg-Tyr-Phe-Tyr-Asn-Ala-Lys-Ala-Gly-Leu-Cys-Gln-Thr-Phe (SEQ ID NO: 22);

$R_3$ is selected from the group

Tyr-Gly-Gly; and

Tyr-Ser-Gly;

$R_4$ is selected from the group

Gly-Asn-Arg-Asn-Asn-Phe-Asp-Thr-Glu-Glu-Tyr-Cys-Ala-Ala-Val-Cys-Gly-Ser-Ala (SEQ ID NO: 23);

Gly-Asn-Arg-Asn-Asn-Phe-Asp-Thr-Glu-Glu-Tyr-Cys-Met-Ala-Val-Cys-Gly-Ser-Ala (SEQ ID NO: 24);

Gly-Asn-Gln-Asn-Arg-Phe-Glu-Ser-Leu-Glu-Glu-Cys-Lys-Lys-Met-Cys-Thr-Arg-Asp (SEQ ID NO: 25);

Gly-Asn-Met-Asn-Asn-Phe-Glu-Thr-Leu-Glu-Glu-Cys-Lys-Asn-Ile-Cys-Glu-Asp-Gly (SEQ ID NO: 26);

Gly-Asn-Glu-Asn-Asn-Phe-Thr-Ser-Lys-Gln-Glu-Cys-Leu-Arg-Ala-Cys-Lys-Lys-Gly (SEQ ID NO: 27);

Gly-Asn-Gly-Asn-Asn-Phe-Val-Thr-Glu-Lys-Glu-Cys-Leu-Gln-Thr-Cys-Arg-Thr-Val (SEQ ID NO: 28);

Gly-Asn-Gly-Asn-Lys-Phe-Tyr-Ser-Glu-Lys-Glu-Cys-Arg-Glu-Tyr-Cys-Gly-Val-Pro (SEQ ID NO: 29);

Gly-Asn-Glu-Asn-Lys-Phe-Gly-Ser-Gln-Lys-Glu-Cys-Glu-Lys-Val-Cys-Ala-Pro-Val (SEQ ID NO: 30);

Gly-Asn-Ser-Asn-Asn-Phe-Leu-Arg-Lys-Glu-Lys-Cys-Glu-Lys-Phe-Cys-Lys-Phe-Thr (SEQ ID NO: 31); and Ala-Lys-Arg-Asn-Asn-Phe-Lys-Ser-Ala-Glu-Asp-Cys-Met-Arg-Thr-Cys-Gly-Gly-Ala (SEQ ID NO: 32);

$Xaa_{11}$ is Pro;
$Xaa_{12}$ is Gly;
$Xaa_{13}$ is selected from the group Pro, Val, Leu, and Trp;
$Xaa_{14}$ is Cys;
$Xaa_{15}$ is Arg or Lys;
$Xaa_{16}$ is Ala;
$Xaa_{17}$ is Met or Leu;
$Xaa_{18}$ is Met or Ile;
$Xaa_{19}$ is Leu, Lys or Arg;
$Xaa_{34}$ is Phe, Val, Ile, or Tyr;
$Xaa_{38}$ is Cys; and
$Xaa_{39}$ is Tyr, Gly, or His.

In a further embodiment polypeptides of the sequence represented by:

$R_1$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$R_2$-$Xaa_{34}$-$R_3$-$Xaa_{38}$-$Xaa_{39}$-$R_4$ where in each case $R_1$ has the sequence:

Val-Arg-Glu-Val-Cys-Ser-Glu-Gln-Ala-Glu (SEQ ID NO: 6)

$R_2$ has the sequence:
Arg-Trp-Tyr-Phe-Asp-Val-Thr-Glu-Gly-Lys-Cys-Ala-Pro-Phe (SEQ ID NO: 14)

$R_3$ has the sequence:
Tyr-Gly-Gly; and $R_4$ has the sequence:
Gly-Asn-Arg-Asn-Asn-Phe-Asp-Thr-Glu-Glu-Tyr-Cys-Ala-Ala-Val-Cys-Gly-Ser-Ala (SEQ ID NO: 23) or Gly-Asn-Arg-Asn-Asn-Phe-Asp-Thr-Glu-Glu-Tyr-Cys-Met-Ala-Val-Cys-Gly-Ser-Ala (SEQ ID NO: 24) are especially preferred. Therefore, polypeptides having the following designations and structural formulas are preferred:

I-18 $R_1$-Pro-Gly-Val-Cys-Arg-Ala-Leu-Ile-Leu-$R_2$-Phe-$R_3$-Cys-Gly-$R_4$ (SEQ ID NO: 43)

I-49 $R_3$-Pro-Gly-Trp-Cys-Arg-Ala-Leu-Ile-Lue-$R_2$-Phe-$R_3$-Cys-Gly-$R_4$ (SEQ ID NO: 44)

I-14 $R_1$-Pro-Gly-Phe-Cys-Arg-Ala-Leu-Ile-Leu-$R_2$-Phe-$R_3$-Cys-Gly-$R_4$ (SEQ ID NO: 45)

I-16 $R_1$-Gly-Gly-Trp-Cys-Arg-Ala-Leu-Ile-Leu-$R_2$-Phe-$R_3$-CYS-Gly-$R_4$ (SEQ ID NO: 46)

where $R_4$ is the sequence identified by SEQ ID NO: 24, and

II-4 $R_1$-Pro-Gly-Pro-Cys-Arg-Ala-Met-Ile-Ser-$R_2$-Phe-$R_3$-Cys-Tyr-$R_4$ (SEQ ID NO: 47)

II-3 $R_1$-Pro-Gly-Trp-Cys-Arg-Ala-Met-Ile-Ser-$R_2$-Ile-$R_3$-Cys-Gly-$R_4$ (SEQ ID NO: 48)

II-6 $R_1$-Pro-Gly-Pro-Cys-Lys-Ala-Met-Ile-Ser-$R_2$-Ile-$R_3$-Cys-Trp-$R_4$ (SEQ ID NO: 49)

III-27 $R_1$-Thr-Gly-Pro-Cys -Arg-Ala-Leu-Ile-Ser-$R_2$-Trp-$R_3$-Cys-Gly-$R_4$ (SEQ ID NO: 50)

III-30 $R_1$-Thr-Gly-Pro-Cys-Arg-Ala-Leu-Ile-Ser-$R_2$-Tyr-$R_3$-Cys-Gly-$R_4$ (SEQ ID NO: 51)

TF7I-VY $R_1$-Pro-Gly-Val-Cys-Arg-Ala-Leu-Ile-Leu-$R_2$-Phe-$R_3$-Cys-Tyr-$R_4$ (SEQ ID NO: 52)

TF7I-LY $R_1$-Pro-Gly-Leu-Cys-Arg-Ala-Leu-Ile-Leu-$R_2$-Phe-$R_3$-Cys-Tyr-$R_4$ (SEQ ID NO: 53)

TF7I-WY $R_1$-Pro-Gly-Trp-Cys-Arg-Ala-Leu-Ile-Leu-$R_2$-Phe-$R_3$-Cys-Tyr-$R_4$ (SEQ ID NO: 54)

TF7I-PG $R_1$-Pro-Gly-Pro-Cys-Arg-Ala-Leu-Ile-Leu-$R_2$-Phe-$R_3$-Cys-Gly-$R_4$ (SEQ ID NO: 55)

IV-47C $R_1$-Pro-Gly-Pro-Cys-Arg-Ala-Met-Met-Lys-$R_2$-Ile-$R_3$-Cys-His-$R_4$ (SEQ ID NO: 56)

IV-54C $R_1$-Pro-Gly-Pro-Cys-Arg-Ala-Leu-Met-Lys-$R_2$-Val-$R_3$-Cys-Tyr-$R_4$ (SEQ ID NO: 57)

IV-31B $R_1$-Pro-Gly-Pro-Cys-Arg-Ala-Leu-Met-Lys-$R_2$-Val-$R_3$-Cys-Phe-$R_4$ (SEQ ID NO: 58)

IV-49C $R_1$-Pro-Gly-Pro-Cys-Arg-Ala-Met-Met-Lys-$R_2$-Ile-$R_3$-Cys-Tyr-$R_4$ (SEQ ID NO: 59)

IV-50C $R_1$-Pro-Gly-Pro-Cys-Arg-Ala-Met-Tyr-Lys-$R_2$-Ile-$R_3$-Cys-Tyr-$R_4$ (SEQ ID NO: 60)

IV-57C $R_1$-Pro-Gly-Val-Cys-Arg-Ala-Met-Met-Lys-$R_2$-Ile-$R_3$-Cys-Gly-$R_4$ (SEQ ID NO: 61)

IV-51C $R_1$-Pro-Gly-Pro-Cys-Lys-Ala-Leu-Met-Arg-$R_2$-Tyr-$R_3$-Cys-Tyr-$R_4$ (SEQ ID NO: 62)

IV-35B $R_1$-Pro-Gly-Pro-Cys-Lys-Ala-Ile-Met-Lys-$R_2$-Ile-$R_3$-Cys-His-$R_4$ (SEQ ID NO: 63)

IV-58C $R_1$-Pro-Gly-Pro-Cys-Lys-Ala-Leu-Met-Lys-$R_2$-Tyr-$R_3$-Cys-His-$R_4$ (SEQ ID NO: 64)

IV-48C $R_1$-Pro-Gly-Pro-Cys-Lys-Ala-Leu-Met-Lys-$R_2$-Trp-$R_3$-Cys-Trp-$R_4$ (SEQ ID NO: 65)

IV-46C $R_1$-Pro-Gly-Pro-Cys-Lys-Ala-Met-Ile-Lys-$R_2$-Leu-R3-Cys-Tyr-$R_4$ (SEQ ID NO: 66)

IV-55C $R_1$-Pro-Gly-Pro-Cys-Lys-Ala-Leu-Met-Lys-$R_2$-Phe-$R_3$-Cys-Tyr-$R_4$ (SEQ ID NO: 67)

IV-32B $R_1$-Pro-Gly-Pro-Cys-Lys-Ala-Leu-Met-Lys-$R_2$-Tyr-$R_3$-Cys-Tyr-$R_4$ (SEQ ID NO: 68)

IV-36B $R_1$-Pro-Gly-Pro-Cys-Lys-Ala-Leu-Met-Lys-$R_2$-Val-$R_3$-Cys-Tyr-$R_4$ (SEQ ID NO: 69)

IV-40B $R_1$-Pro-Gly-Ala-Cys-Lys-Ala-Met-Tyr-Lys-$R_2$-Ile-$R_3$-Cys-Gly-$R_4$ (SEQ ID NO: 70)

53b $R_1$-Pro-Gly-Pro-Gly-Arg-Ala-Leu-Ile-Leu-$R_2$-Phe-$R_3$-Ala-Tyr-$R_4$ (SEQ ID NO: 71)

and TF71-IC $R_1$-Pro-Gly-Pro-Cys-Arg-Ala-Leu-Ile-Leu-$R_2$-Phe-$R_3$-Cys-Tyr-$R_4$ (SEQ ID NO: 72)

where $R_4$ is the sequence identified by SEQ ID NO: 23. However, as noted, according to the invention, $R_1$ can be any peptide having from 5 to 250 amino acids residues wherein at least one residue is a Cys. In specific embodiments $R_1$ is selected from the group consisting of (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), or (SEQ ID NO: 13). $R_2$ can be any peptide having 14 amino acids wherein at least one residue is a Cys. In specific embodiments, $R_2$ is selected from the group consisting of (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22). $R_3$ is a tripeptide, especially a tripeptide selected from the group consisting of Tyr-Gly-Gly, or Tyr-Ser-Gly. $R_4$ can be any peptide having 12 to 250 amino acids wherein at least one residue is a Cys. In specific embodiments $R_4$ is selected from the group consisting of (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32).

The present invention also contemplates polypeptides where, in addition to the changes noted above, the residues corresponding to residue 20, 44 and 46 of APPI are modified. According to this aspect of the present invention, amino acid substitutions that promote the favorable interaction between the polypeptide and the particular serine protease of the coagulation cascade are contemplated. According to this aspect of the present invention residue 20, which is equivalent to the first amino acid residue of $R_2$, is modified. Preferably, according to this aspect of the invention the amino acid at position 20 of APPI is modified to Ala, Val, Ser, Thr, Asn, Gln, Asp, Glu, Leu, or Ile. Therefore, variants wherein the first amino acid of R$_2$, is represented by Xaa$_{20}$, where Xaa$_{20}$ is selected from the group consisting of Ala, Val, Ser, Thr, Asn, Gln, Asp, Glu, Leu, and Ile are preferred.

According to this aspect of the present invention residues 44 and 46 of APPI which are equivalent to the fifth and the seventh residues of R$_4$ are modified to promote the favorable interaction between the polypeptide and the particular serine protease of the coagulation cascade such as the tissue factor-factor VIIa complex. Therefore, polypeptides where positions 44 and 46, represented by Xaa$_{44}$ and Xaa$_{46}$, respectively, are modified to promote the favorable interaction between the polypeptide and tissue factor-factor VIIa complex are preferred. Exemplary residues at Xaa$_{46}$ include Asp or Glu. Other substitutions will be apparent to one of skill in the art based on the teachings of the instant application. The resulting polypeptide has an apparent K$_i$ with respect to Tissue Factor-Factor VIIa of less that about 100 nM, more preferable less that 10 nM and most preferably 3 nM or lower. Optionally, the polypeptide also has an apparent K$_i$* with respect to both Factor XIa and kallikrein of less than about 10 nM and most preferably 2 nM or lower.

In a further embodiment, the present invention encompasses a composition of matter comprising isolated nucleic acid, preferably DNA, encoding the protein component of a composition of matter comprising a polypeptide represented by Structural Formula I. The invention further comprises an expression control sequence operably linked to the DNA molecule, an expression vector, preferably a plasmid, comprising the DNA molecule, where the control sequence is recognized by a host cell transformed with the vector, and a host cell transformed with the vector:

Preferred expression vectors of the present invention may be selected from; pBR322, phGH1, pBO475, pRIT5, pRIT2T, pKK233-2, pDR540, and pPL-lambda, with the most preferred vector being pSAlzl.

Preferred host cells containing the expression vector of the present invention may be selected from E. coli K12 strain 294 (ATCC No. 31446), E. coli strain JM101, E. coli B, E. coli X1776 (ATCC No. 31537), E. coli c600, E. coli W3110 (F-, gamma-, prototrophic, ATCC No. 27325), Bacillus subtilis, Salmonella typhimurium, Serratia marcesans, and Pseudomonas species, with the most preferred host cell being E. coli W3110 (ATCC No. 27325), or a derivative thereof such as the protease deficient strain 27C7.

The composition of the present invention may be made by a process which includes the steps of isolating or synthesizing nucleic acid sequences encoding any of the amino acid sequences described above, ligating the nucleic acid sequence into a suitable expression vector capable of expressing the nucleic acid sequence in a suitable host, transforming the host with the expression vector into which the nucleic acid sequence has been ligated, culturing the host under conditions suitable for expression of the nucleic acid sequence, whereby the protein encoded by the selected nucleic acid sequence is expressed by the host. In this process, the ligating step may further contemplate ligating the nucleic acid into a suitable expression vector such that the nucleic acid is operably linked to a suitable secretory signal, whereby the amino acid sequence is secreted by the host. The secretory signal may be selected from the group consisting of the leader sequence of stII, lamB, herpes gD, lpp, alkaline phosphatase, invertase, and alpha factor and is preferably stII.

The present invention further extends to therapeutic applications for the compositions described herein. Thus the invention includes a pharmaceutical composition comprising a pharmaceutically acceptable excipient and a purified amino acid sequence represented by Formula I.

Those applications include, for example, a method for inhibiting thrombus formation in a mammal comprising administering a pharmaceutically effective amount of the pharmaceutical composition to the mammal. The pharmaceutically effective amount may be between about 0.001 nM and 1.0 mM, is preferably between about 0.1 nM and 100 μM, and is most preferably between about 1.0 nM and 50 μM. Additionally, the pharmaceutical composition may be administered prior to, following, or simultaneously with administration of a fibrinolytic or thrombolytic agent such as tissue plasminogen activator, streptokinase, urokinase, prourokinase, and modifications thereof. Alternatively the pharmaceutical composition may be administered in combination with an anticoagulant.

Additionally, other applications include, for example, a method of treating a mammal for which inhibiting Factor VIIa, Factor XIa, plasma kallikrein, or plasmin is indicated comprising administering a pharmaceutically effective amount of the pharmaceutical composition to the mammal. Such indications include; inflammation, septic shock, hypotension, ARDS, DIC, cardiopulmonary bypass surgery, and bleeding from postoperative surgery.

BRIEF DESCRIPTION OF THE FIGURES

FIG. 2. Sequence alignment of Kunitz domains from mammalian sources. Aligned are TF7I-C (residues 1–58) (SEQ ID NO: 33), which is described herein; APPI (residues 1–58) (SEQ ID NO: 34) from human Alzheimer's disease amyloid β-protein precursor, residues 287–344 (Castro, M. et al. FEBS Lett. 267:207–212 [1990]); TFPI-KD1 (residues 22–79) (SEQ ID NO: 35), TFPI-KD2 (residues 93–150) (SEQ ID NO: 36), and TFPI-KD3 (residues 185–242) (SEQ ID NO: 37) of human TFPI, respectively (Broze Jr., G. J. et al., Biochemistry 29:7539–7546 [1990]); ITI-KD1 and ITI-KD2, (residues 22–79 and 78–135) (SEQ ID NO: 38 and 39) of human inter-α-trypsin inhibitor, respectively (Vetr, H. et al., FEBS Lett. 245:137–140 [1989]); Collagen α 3 (VI) (residues 2899–2956) (SEQ ID NO: 40) Collagen alpha 3 (VI) chain precursor (Chu, M. L. et al. EMBO J. 9:385–393 [1990]); HKIB9 (7–60) (SEQ ID NO: 41) Human Kunitz-type protease inhibitor, HKIB9 (Norris, K., in Genbank Database (Dec. 31, 1993, Release 39.0), submitted Jan. 19, 1994); BPTI (1–58) (SEQ ID NO: 42), Aprotinin, bovine basic pancreatic trypsin inhibitor (Creighton T. E. and Charles, I. G., Cold Spring Harbor Symp. Quant. Biol. 52:511–519 [1987]). A motif alignment of invariant residues is listed.

FIGS. 4A and 4B. Sequence and Apparent Equilibrium Dissociation Constants for Kunitz Domain Variants. Amino acids positions corresponding to those in APPI are indicated.

DETAILED DESCRIPTION OF THE INVENTION

A. Definitions

Figure 1:
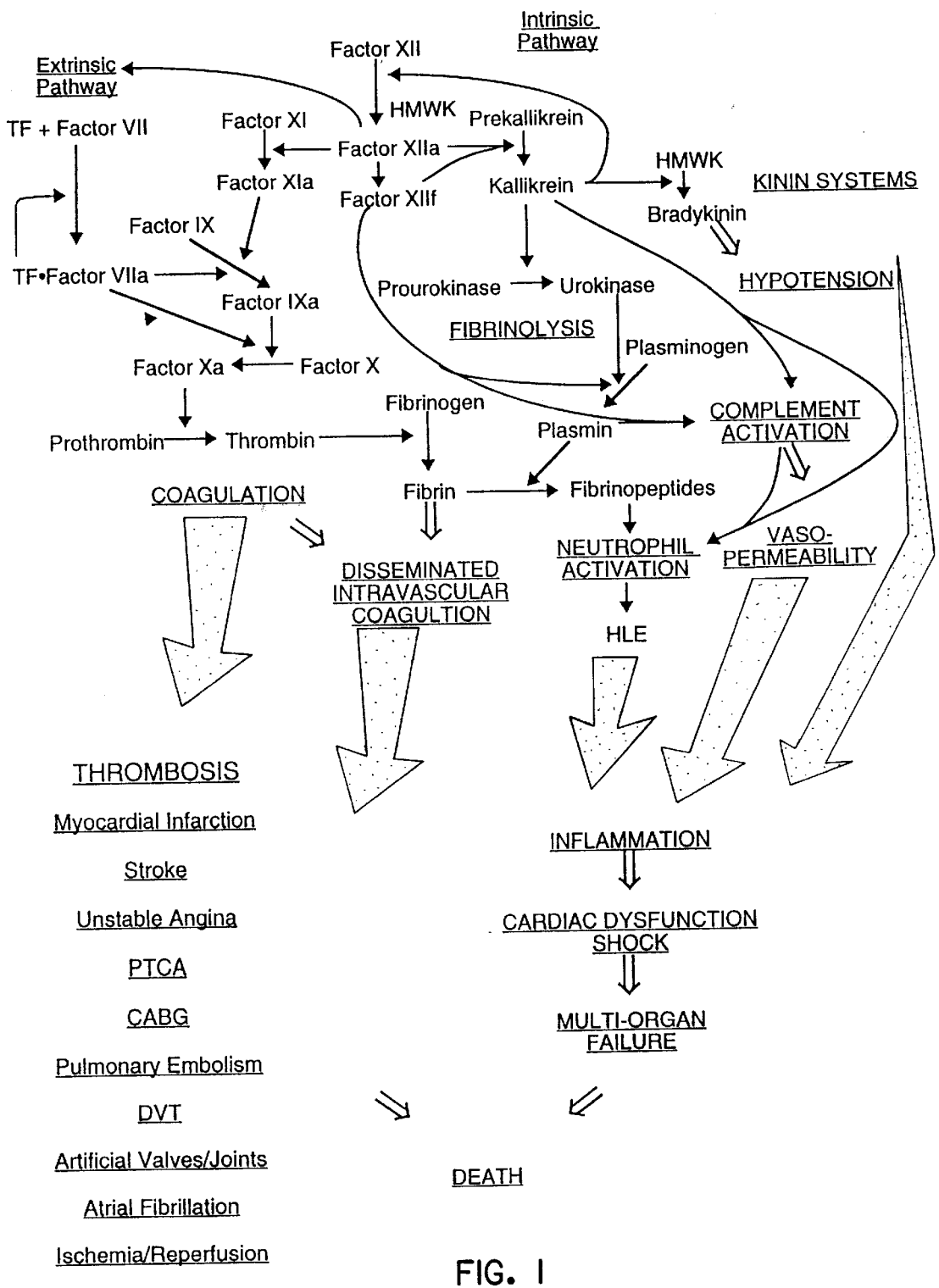
FIG. 1. Schematic outline of selected enzymes and mediators that modulate the coagulation, contact, fibrinolytic, inflammatory, and complement pathways. Activation of these pathways can lead to the clinical states indicated.

Terms used in the claims and specification are defined as set forth below unless otherwise specified.

The term amino acid or amino acid residue, as used herein, refers to naturally-occurring L α-amino acids or residues, unless otherwise specifically indicated. The commonly used one- and three-letter abbreviations for amino acids are use herein (Lehninger, A. L., *Biochemistry*, 2d ed., pp. 71–92, Worth Publishers, N.Y. [1975], ).

When referring to mutants or variants, the wild type amino acid residue is followed by the residue number and the new or substituted amino acid residue. For example, substitution of P for wild type T in residue position 11 is denominated T11P.

The $P_1$ residue refers to the position proceeding the scissile peptide bond of the substrate or inhibitor as defined by Schechter and Berger (Schechter, I. and Berger, A., *Biochem. Biophys. Res. Commun.* 27:157–162 [1967]).

"Expression vector" refers to a DNA construct containing a DNA sequence which is operably linked to a suitable control sequence capable of effecting the expression of the protein encoded by the DNA in a suitable host. Such control sequences generally include a promoter to effect transcription, an optional operator sequence to control transcription, a sequence encoding suitable mRNA ribosome binding sites, and sequences which control termination of transcription and translation. The vector may be a plasmid, a phage particle or "phagemid", or simply a potential genomic insert. Once transformed into a suitable host, the vector may replicate and function independently of the host genome, or may, in some instances, integrate into the genome itself. In the present specification, "plasmid", "vector" and "phagemid" are sometimes used interchangeably as the plasmid is the most commonly used form of vector at present. However, the invention is intended to include such other forms of expression vectors which serve equivalent functions and which are, or which become, known in the art.

"Operably linked," when describing the relationship between two DNA or polypeptide sequences, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The abbreviations used herein are: TF, tissue factor; FVIIa, Factor VIIa; TFPI, tissue factor pathway inhibitor; ATIII, Antithrombin III; FXa, Factor Xa; FXIa, Factor XIa; FXIIa, Factor XIIa; APPI, Alzheimer's amyloid β-protein precursor inhibitor; $TF_{1-243}$, *E. coli* derived recombinant human tissue factor encompassing residues 1–243; BPTI, basic pancreatic trypsin inhibitor; $K_i^*$, apparent equilibrium dissociation constant; CHAPS, 3-[(3-cholamidopropyl) dimethylammonio]-1-propanesulfonate; PBS, phosphate buffered saline; BSA, bovine serum albumin; HPLC, high performance liquid chromatography; PT, prothrombin time; APTT, activated partial thromboplastin time.

B. Discovery and Preferred Embodiments

The present inventors have discovered that substitutions at certain key amino acid positions within and around the primary and secondary binding loops of Kunitz domain serine protease inhibitors can dramatically improve the potency of the inhibitors toward the tissue factor-FVIIa complex. The present invention therefore provides for polypeptides which comprise one or more of these mutant Kunitz domains serine protease inhibitors. According to the present invention specific amino acid residues of APPI and other Kunitz domain proteins are altered to provide novel serine protease inhibitors. The Kunitz domain mutants can comprise a portion of any of a number of proteins to provide a protein that can inhibit tissue factor-FVIIa as well as other serine proteases of the coagulation cascade. For instance, the Kunitz domain mutants of the instant invention can replace the Kunitz domain of other proteins known to have Kunitz domains to provide for novel polypeptides which can inhibit tissue factor-FVIIa as well as other serine proteases of the coagulation cascade.

According to the present invention, residues 11–19, 34, and 38–39 were altered by Kunkel mutagenesis as described in Example 1. Variants were then assayed for their ability to inhibit TF-FVIIa and several other serine proteases. The best TF-FVIIa Kunitz domain inhibitors showed a strong preference for Arg and Lys in position 15; however proteins with Met at position 15 were also inhibitors. As expected, Gly at position 12 and Ala at position 16 produced the best inhibitors (see FIG. 4). Gly is almost always found at residue 12 in Kunitz domains (Creighton, T. E. and I. G. Charles, *Cold Spring Harbor Symp. Quant. Biol.* 52:511–519 [1987]). Position 16 is usually either Gly or Ala in Kunitz domains (Creighton, T. E. and I. G. Charles, *Cold Spring Harbor Symp Quant Biol* 52:511–519 [1987]). In addition, maintaining Cys at positions 14 and 38 generally led to better inhibitors but its requirement was not absolute.

The most preferred residues at other positions in the binding loop were Pro at position 11, Leu and Met at position 17, Met and Ile at position 18, and Leu or Lys at position 19. However, inhibition of TF-FVIIa was also observed when residues Arg, Ala, Glu, Gly, or Thr at position 11, Ile, Arg, Tyr, or Ser at position 17, Leu, Tyr, His, or Phe at position 18, and Arg, Ala, or Ile at position 19 were incorporated into the Kunitz domain. A number of residues were most preferable at position 34 including Val, Ile and Tyr. Other residues here included Leu, Phe, Trp, and Ser. The residues at positions 13 and 39, which are in close proximity to one another (Hynes, T. R. et al., *Biochemistry*

Figure 3:
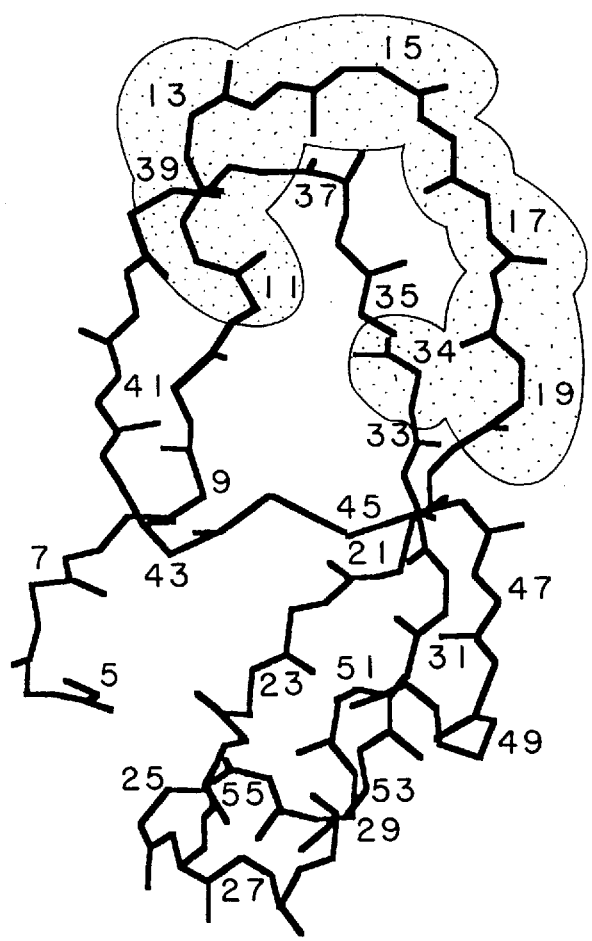
FIG. 3. Model of APPI and other Kunitz domains. The numbers refer to the residues found in APPI and other Kunitz domains; residue 15 corresponds to the P$_1$ residue. The shaded area refers to the primary (residues 11–19) and secondary (residues 34–39) binding loops of APPI and other Kunitz domains.

29:10018–10022 [1990]) (see FIG. 3), also affected TF-FVIIa inhibitory activity. Most preferred residues at position 39 included Gly and Tyr; Trp, Phe, and His were also preferred. When Gly was present at position 39, the residue at position 13 had a significant effect on TF-FVIIa inhibition; large hydrophobic amino acids at position 13 were about 4-fold more potent than Pro at this position. When Tyr was present at position 39, the most potent inhibitors were found ($K_i$*=2–3 nM) and the residue at position 13 made little difference in binding affinity. Therefore, with respect to potent inhibition of TF-FVIIa, hydrophobic residues at either or both positions 13 and 39 are preferred; elimination of these favorable interactions leads to less potent inhibitors.

Several inhibitors in FIG. 4 represent Kunitz domain inhibitors that are able to potently inhibit TF-FVIIa in the absence of FXa. For example, the TF7I-C variant differs by 4 key amino acids (Thr11Pro, Met17Leu, Ser19Leu and Gly39Tyr) compared to wild type APPI and results in an increase in affinity for the TFF-VIIa complex of greater than 150-fold. BPTI has recently been shown to competitively inhibit TF-FVIIa activity, albeit with relatively weak affinity ($K_i$=30 μM) (Chabbat, J. et al., *Thromb Res* 71:205–215 [1993]). In addition, the first Kunitz domain of TFPI itself does not potently inhibit TF-FVIIa, having a $K_i$* of ca. 600 nM.

The increased affinity of TF7I-C for TF-FVIIa relative to APPI is reflected in its ability to prolong the clotting time in a prothrombin time assay (FIG. 6). At 40 μM, APPI had little effect (1.5-fold prolongation), whereas TF7I-C prolonged the clotting time initiated by TF membranes by 3.5-fold. BPTI has recently been shown to inhibit TF-induced coagulation; however, ca. 75 μM was needed to prolong the clotting time 1.4-fold in a PT assay (van den Besselaar, A. M. H. P. et al., *Thromb Haemostas* 69:298–299 [1993]).

Interestingly, many of the inhibitors that resulted in increased binding affinity for TF-FVIIa, also resulted in more potent inhibitors of FXIa and kallikrein. This implies that the active sites of FVIIa and FXIa are somewhat alike, which may not be too surprising since Factor IX is a substrate for both proteases. APPI is a potent inhibitor of FXIa (Wagner, S. L. et al., *Biochem. Biophys. Res. Commun.* 186:1138–1145 [1992]). Inhibition of kallikrein was unexpected and suggests that the active site of kallikrein may also be similar. In contrast, TF7I-C, for example, did not inhibit thrombin, Factor XIIa or activated protein C (Ki*>10 μM) and only poorly inhibited FXa (Ki*=90 nM) and plasmin (Ki*=40±6 nM). TF7I-C is much more effective than APPI at prolonging the clotting time in the APTT assay, a measure of the intrinsic coagulation pathway (FIG. 7). This is consistent with more potent inhibition of FXIa and kallikrein by TF7I-C compared to APPI. Much higher concentrations of inhibitor (>100 Ki*) are required to prolong clotting times in the plasma assays compared to the conditions required for potent inhibition in vitro. Possible explanations include suboptimal binding conditions provided in the in vitro clotting assays, solution vs. membrane bound inhibition of proteases, kinetics of inhibition, and cross reactivity with other plasma serine proteases.

On the other hand, several inhibitors in FIG. 4 resulted in specific inhibition of TF-FVIIa with Ki*>100 nM for FXIa and kallikrein. These inhibitors generally had Lys present at position 19 and Met at position 18. At position 19, Lys or Arg are preferred for specific inhibition of TF-FVIIa. Although their ability to inhibit FXIa and kallikrein has been reduced, they are still potent inhibitors of TF-FVIIa (see FIG. 4).

According to the present invention, residues 20 and 46, as well as residue 44, in addition to the putative contact residues in the primary binding loop (residues 11–19) and secondary binding loop (residues 34, 38 and 39), (see FIG. 2) of APPI have been identified as key residues. In addition to information derived from the x-ray crystal structures of serine proteases with Kunitz domain inhibitors, the amino acid sequences of trypsin and the serine protease domain of FVIIa can be aligned to study the potential interactions between FVIIa and APPI. The variable region 2 (residues 59–62; chymotrypsinogen numbering system, see, for example, Greer, J., (1990) Proteins 7:317–334) in FVIIa contains 8 residues compared to only 3 in trypsin. Without being limited to any one theory, this may allow this surface loop to make contact with a bound Kunitz domain. In FVIIa, residue 59b of this loop is a Lys, which, without limitation to a theory, may sterically overlap with residue Arg20 in APPI. This is an unfavorable interaction (both sterically and electrostatically). In the APPI crystal structure, the surface residue, Arg20 is remarkably well defined probably due to the packing of other side chains in APPI, suggesting, without limitation to one theory, that rotation to avoid collision with Lys59b in FVIIa is improbable. Without reliance on any one theory, residue 59b in FVIIa, in contrast, can probably freely rotate which may put it in favorable contact with Asp46 of APPI or an appropriate residue at position 18 in APPI. In addition, position 18 of APPI is also near FVIIa (Lys59b) and APPI (Arg20) and may play a role in these binding interactions.

Based on these observations, residues 20 and 44, and 46 of APPI Kunitz domain or a polypeptide as described herein are modified. According to this aspect of the present invention Arg20 may be modified to Ala, Val, Ser, Thr, Asn, Gln, Asp, Glu, Leu, or Ile. At residue 46 any hydrogen bond acceptor may be substituted for Asp. In one embodiment either Asp or Glu are found at position 46. Residues at position 44 as well as position 20 and 46, as well as the residues of the primary and secondary binding loops are all meant to promote favorable interactions between Kunitz domain proteins and the tissue factor-Factor VIIa complex. Such favorable interaction can be assessed according to those assays described herein for the measurement of apparent $K_i$* with respect to tissue factor-Factor VIIa.

C. Utility

As previously indicated, many common human disorders are characteristically associated with a hypercoagulable state leading to intravascular thrombi and emboli (*Thrombosis in Cardiovascular Disorders,* (Fuster, V. and Verstraete, M., eds.), W. B. Saunders, Philadelphia [1992]). These are a major cause of medical morbidity, leading to phlebitis, infarction, and stroke, and of mortality, from stroke and pulmonary and cardiac emboli. A large percentage of such patients have no antecedent risk factors, and develop venous thrombophlebitis and subsequent pulmonary emboli without a known cause. Other patients who form venous thrombi have underlying diseases known to predispose to these syndromes.

Some of these patients may have genetic or acquired deficiencies of factors that normally prevent hypercoagulability, such as antithrombin III. Others have mechanical obstructions to venous flow, such as tumor masses, that lead to low flow states and thrombosis. Patients with malignancy have a high incidence of thrombotic phenomena, for unclear reasons. Antithrombotic therapy in this situation with currently available agents is dangerous and often ineffective.

Patients with atherosclerosis are predisposed to arterial thromboembolic phenomena for a variety of reasons. Atherosclerotic plaques form niduses for platelet plugs and thrombi that lead to vascular narrowing and occlusion, resulting in myocardial and cerebral ischemic disease. Thrombi that break off and are released into the circulation can cause infarction of different organs, especially the brain, extremities, heart and kidneys. After myocardial infarctions, clots can form in weak, poorly functioning cardiac chambers and be released into the circulation to cause emboli. All such patients with atrial fibrillation are felt to be at great risk for stroke and require antithrombotic therapy.

In addition, thrombolytic therapy for acute myocardial infarction has become an established procedure for patients (Collen, D. and Stump, D., *Ann Rev Med.* 39:405–423 [1988]). However, currently available thrombolytic agents are not effective in all patients which is manifest by reocclusion, resistance to reperfusion, prolonged times to achieve normal coronary flow and the like.

Patients whose blood flows over artificial surfaces, such as prosthetic synthetic cardiac valves or hip replacements, or through extracorporeal perfusion devices, are also at risk for the development of platelet plugs, thrombi, and emboli. It is standard practice that patients with artificial cardiac valves be chronically anti-coagulated.

Thus, a large category of patients, including those with cancer, atherosclerosis, coronary artery disease (PTCA, CABG, Post MI, etc.), unstable angina, artificial heart valves, and a history of stroke, transient ischemic attacks, atrial fibrillation, deep vein thrombosis, phlebitis, or pulmonary emboli, are candidates for limited or chronic antithrombotic therapy. However, this therapy is often ineffective or morbid in its own right. This is partially because the number of available therapeutic agents is limited. Available anti-platelet agents, such as aspirin, inhibit the cyclooxygenase-induced activation of platelets only and are often inadequate for therapy. Available anticoagulants include heparin and warfarin which are not always efficacious and can often have side effects including increased bleeding risk and problems associated with monitoring these therapies.

An agent which effectively inhibits the formation of fibrin from fibrinogen should accordingly be particularly useful in therapeutic intervention in a large group of disorders characterized by a hypercoagulable state.

As a general matter, however, in the management of thromboembolic and inflammatory disorders, the compounds of the present invention may be utilized in compositions with a pharmaceutically acceptable excipient for injectable administration, in compounds such as tablets, capsules, or elixirs for oral administration. Animals in need of treatment using compounds of the present invention can be administered dosages that will provide optimal efficacy. The dose and method of administration will vary from animal to animal, and be dependent upon such factors as weight, diet, concurrent medication, and other factors which those skilled in the medical arts will recognize.

There are many approaches to the regulation of blood coagulation ranging from the currently used nonspecific inhibitors warfarin and heparin, to more selective agents, such as thrombin or FXa inhibitors. FVIIa, FXIa, and plasma kallikrein represent other targets for regulation of blood coagulation since they can either initiate or contribute to coagulation by the extrinsic or intrinsic pathway. The zymogens are present in plasma at lower concentrations than prothrombin and their effects upon hemostasis are considerably amplified. Thus inhibitors of these enzymes should be very potent, since any uninhibited enzyme can contribute to further activation of the cascade. The current anticoagulant therapies (heparin, warfarin) are nonspecific inhibitors. Specific inhibitors may be advantageous with respect to side effects such as bleeding. On the other hand coordinate inhibition of several proteases may be desirable for certain indications. The regulation of coagulation and its relationship to disease is a very complex process.

TF-FVIIa is an appropriate target for the intervention in coagulation processes because it is thought to initiate the cascade (see FIG. 1) (Broze Jr., G. J. et al., *Biochemistry* 29:7539–7546 [1990; Broze Jr., G. J., *Semin. Hematol.* 29:159–169 [1992]). Thus, the inhibition of FVIIa, FXIa, and/or plasma kallikrein by agents described herein represents an approach for clinical intervention in various thrombotic disorders. Thus the agents described herein are useful in the treatment of thrombosis. More specifically, the instant inhibitors are especially useful as adjunct therapy for thrombolysis, unstable angina, deep vein thrombosis, hip replacement, coronary artery bypass graft, percutaneous transluminal coronary angioplasty, pulmonary embolism, septic shock, and DIC.

The agents described herein are also useful in the treatment of diseases where intervention in the activation of the contact pathway or neutrophil activation is indicated (e.g. inflammation, coagulation, fibrinolysis, and complement activation). More specifically, the instant inhibitors are especially useful in the treatment of diseases where inhibition of FXIa, kallikrein, FXIIa, FXa, and HLE, complement is indicated (see FIG. 1) as for example in the treatment of sepsis or septic shock, inflammation, ARDS, DIC, hypotension, cardiopulmonary bypass surgery, and for bleeding from postoperative surgery.

The agents described herein may be useful in clinical situations that require acute or chronic therapy. It is anticipated that indications for which acute therapy is indicated are more preferred than those for chronic therapy. The pharmaceutical use of foreign or mutant human proteins may be immunogenic; however foreign proteins are used to treat acute indications. An example of such a protein is streptokinase, a protein derived from streptococci that acts as a fibrinolytic and is commonly used to treat acute myocardial infarction. The agents described herein may elicit an immune response; however related foreign proteins such as EPTI have been used in humans clinically and are not anticipated to elicit a serious immune response. The covalent attachment of polyethylene glycol (PEG) to the agents described herein may reduce the immunogenicity and toxicity, and prolong the half-life as has been observed with other proteins (Katre N. V., *J. Immunol.* 144:209–213 [1990]; Poznansky, M. J. et al., *FEB* 239:18–22 [1988]; Abuchowski, A. et al., *J. Biol. Chem.* 252:3582–3586 [1977])

D. Methods of Making

Chemical Synthesis

One method of producing the Kunitz domain polypeptides of Formula I involves chemical synthesis of the protein, followed by treatment under oxidizing conditions appropriate to obtain the native conformation, that is, the correct disulfide bond linkages. This can be accomplished using methodologies well known to those skilled in the art (see Kelley, R. F. and Winkler, M. E. in *Genetic Engineering Principles and Methods*, (Setlow, J. K., ed.)., Plenum Press, N.Y., vol. 12, pp. 1–19 [1990]; Stewart, J. M. and Young, J.

D. *Solid Phase Peptide Synthesis* Pierce Chemical Co. Rockford, Ill. [1984]).

Polypeptides of the invention, especially those containing 58 amino acid residues or fewer, may be prepared using solid phase peptide synthesis (Merrifield, *J. Am. Chem. Soc.,* 85:2149 [1964]; Houghten, *Proc. Natl. Acad. Sci. U.S.A.* 82:5132 [1985]). Solid phase synthesis begins at the carboxy-terminus of the putative peptide by coupling a protected amino acid to a suitable resin, as shown in FIGS. 1-1 and 1-2, on pages 2 and 4 of Stewart and Young supra.

In synthesizing polypeptides of this invention, the carboxyl terminal amino acid, with its α-amino group suitably protected, is coupled to a chloromethylated polystyrene resin (see FIG. 1-4, page 10 of Stewart and Young supra.). After removal of the α-amino protecting group with, for example, trifluoroacetic acid (TFA) in methylene chloride and neutralizing in, for example TEA, the next cycle in the synthesis is ready to proceed.

The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxytris (dimethylamino) phosphonium hexafluorophosphate] method, N-hydroxysuccinic acid imido ester method, etc.), and Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the α-and ε-amino side chain groups are exemplified by benzyloxycarbonyl (abbreviated Z), isonicotinyloxycarbonyl (iNOC), O-chlorobenzyloxycarbonyl [Z(NO$_2$)], p-methoxybenzyloxycarbonyl [Z(OMe)], t-butoxycarbonyl, (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

As protective groups for carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2, 4, 6-trimethy-benzyl (Tmb) etc, and the hydroxyl group in the serine can be protected with benzyl, t-butyl, acetyl, tetrahydropyranyl etc.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 µM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Kunitz domains can be made either by chemical synthesis, described above, or by semisynthesis. The chemical synthesis or semisynthesis methods of making allow the possibility of non-natural amino acid residues to be incorporated. This has been carried out for Kunitz domains and related proteins as previously described (Beckmann, J. et al., *Eur. J. Biochem.* 176:675–682 [1988]; Bigler, T. L. et al., *Prot. Sci.* 2:786–799 [1993]).

Gene Synthesis, Cloning, and Expression

General Procedures From the amino acid sequence, as provided in Formula I, the purified protein may be produced using standard recombinant DNA techniques. These techniques contemplate, in simplified form, taking a gene encoding the Kunitz domain polypeptides of Formula I; inserting it into an appropriate vector; inserting the vector into an appropriate host cell; culturing the host cell to cause expression of the Kunitz domain polypeptides of Formula I; and purifying the protein produced thereby.

Somewhat more particularly, the DNA sequence encoding the Kunitz domain polypeptides of Formula I is cloned and manipulated so that it may be expressed in a convenient host. DNA encoding Formula I polypeptides can be obtained by synthetically constructing the DNA sequence (Sambrook, J. et al., *Molecular Cloning* (2nd ed.), Cold Spring Harbor Laboratory, N.Y. [1989]).

The DNA encoding Formula I peptides is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, *E. coli* may be transformed using pBR322, a plasmid derived from an *E. coli* species (Mandel, M. et al., *J. Mol. Biol.* 53:154 [1970]).

Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

Direct expression of the Kunitz domain polypeptides of Formula I A preferred vector is pSAlzl. This vector was created as described in Example 1 and contains origins of replication for *E. coli,* the alkaline phosphatase promoter, the stII signal sequence and APPI variant gene, and the ampicillin resistance gene. Other preferred vectors are pBO475, pRIT5 and pRIT2T (Pharmacia Biotechnology). These vectors contain appropriate promoters followed by the Z domain of protein A, allowing genes inserted into the vectors to be expressed as fusion proteins. Further discussion of these vectors may be found below.

Other preferred vectors can be constructed using standard techniques by combining the relevant traits of the vectors described herein. Relevant traits of the vector include the promoter, the ribosome binding site, the APPI variant gene or gene fusion (the Z domain of protein A and APPI variant and its linker), the signal sequence, the antibiotic resistance markers, the copy number, and the appropriate origins of replication.

In *E. coli*, Kunitz domains have been expressed as intact secreted proteins (Castro, M. et al., *FEBS Lett.* 267:207–212 [1990]), intracellularly expressed proteins (Altman, J. D. et al., *Protein Eng.* 4:593–600 [1991]), or as fusion proteins (Sinha, S. et al., *J. Biol. Chem.* 266:21011–21013 [1991]; Lauritzen, C. et al., *Prot. Express. Purif.* 2:372–378 [1991]; Auerswald, E. A. et al., *Biol. Chem. Hoppe-Seyler* 369: 27–35 [1988]).

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis,* and other enterobacteriaceae such as *Salmonella-typhimurium* or *Serratia marcesans,* and various pseudomonas species. The preferred prokaryote is *E. coli* W3110 (ATCC 27325). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (Tissue Culture, Academic Press, Kruse and Patterson, eds. [1973]). Examples of such useful host cell lines are VERO and HeLa cells, Chinese Hamster Ovary (CHO) cell lines, W138, 293, BHK, COS-7 and MDCK cell lines. Yeast expression systems have been used to make Kunitz domains (Wagner, S. L. et al., *Biochem. Biophys. Res. Commun.* 186:1138–1145 [1992]; Vedvick, T. et al., *J. Indust. Microbiol.* 7:197–202 [1991]). In particular the yeast *Pichia pastoris* has been used successfully using the *Saccharomyces cerevisiae* α mating factor prepro signal sequence and the *P. pastoris* alcohol oxidase AOX1 promoter and terminator sequences. Other yeast expression vectors and hosts commonly used to express heterologous proteins are also contemplated.

Gene Fusions A variation on the above procedures contemplates the use of gene fusions, wherein the gene encoding the APPI variant is associated, in the vector, with a gene encoding another protein or a fragment of another protein. This results in the APPI variant being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering,* (Williamson, R., ed.), Academic, London, Vol. 4, p. 127 [1983]; Uhlen, M. and Moks, T., *Methods Enzymol.* 185:129–143 [1990]). Protein A fusions are often used because the binding of protein A, or more specifically the Z domain of protein A, to IgG provides an "affinity handle" for the purification of the fused protein (Nilsson, B. and Abrahmsen, L. *Methods Enzymol.* 185:144–161 [1990]). It has also been shown that many heterologous proteins are degraded when expressed directly in *E. coli,* but are stable when expressed as fusion proteins (Marston, F. A. O., *Biochem J.* 240:1 [1986]).

APPI variants expressed as fusion proteins may be properly folded or may require folding to obtain the native structure. The properly folded fusion protein may be active and useful as a serine protease inhibitor. More preferred would be the correctly folded native protein that is obtained from the fusion protein by methods known in the art. Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the APPI variant gene.

Alternatively, one can employ proteolytic cleavage of fusion proteins, which has been recently reviewed (Carter, P.

in *Protein Purification: From Molecular Mechanisms to Large-Scale Processes,* (Ladisch, M. R., Willson, R. C., Painton, C. C., and Builder, S. E., eds.), American Chemical Society Symposium Series No. 427, Ch 13, pp. 181–193 [1990]).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as an APPI variant. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The protein may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the protein is treated with a chaotrope, such a guanidine HCl, and is then treated with a redox buffer, containing, for example, reduced and oxidized dithiothreitol or glutathione at the appropriate ratios, pH, and temperature, such that the protein of interest is refolded to its native structure.

Mutant DNA Production As previously discussed, various techniques are also available which may now be employed to produce mutant APPI DNA, which encodes for additions, deletions, or changes in amino acid sequence of the resultant protein relative to the parent APPI molecule.

By way of illustration, with expression vectors encoding APPI in hand, site specific mutagenesis (Kunkel et al., *Methods Enzymol.* 204:125–139 [1991]; Carter, P., et al., *Nucl. Acids. Res.* 13:4331 [1986]; Zoller, M. J. et al., *Nucl. Acids Res.* 10:6487 [1982]), cassette mutagenesis (Wells, J. A., et al., *Gene* 34:315 [1985]), restriction selection mutagenesis (Wells, J. A., et al., *Philos. Trans, R. Soc. London SerA* 317, 415 [1986]) or other known techniques may be performed on the APPI DNA. The mutant DNA can then be used in place of the parent DNA by insertion into the aforementioned expression vectors. Growth of host bacteria containing the expression vectors with the mutant DNA allows the production of mutant APPI (i.e., analogs or homologs of APPI), which can be isolated as described herein.

Purification and characterization Purification and characterization of APPI variants may be carried out by any art standard technique including gel filtration, ion exchange, hydrophobic interaction, and affinity chromatography. In the instant case, recombinant APPI variants were purified from the media of *E. coli* grown in 10 l fermentors or shake flasks by chromatography on a trypsin affinity column followed by reverse phase C18 HPLC.

Following site-directed mutagenesis of the APPI gene and confirmation of clones by DNA sequence analysis, variant proteins were expressed in and purified from *E. coli*. The Kunitz domains were concentrated and partially purified from the media using a trypsin affinity column. The final purification was carried out using reverse phase C18 HPLC as described in Example 2. The expression level of most of the variants was ca. 1 mg/L in shake flasks and 80–100 mg/L in 10 L fermentations. Following purification, protein sequences were verified by mass spectrometry for the correct mass predicted from the sequence, assuming that all three disulfides were formed; all were within the error of this measurement (±2 amu). HPLC chromatographs of inhibitors containing a Met commonly displayed a small peak eluting just before or just after the major inhibitor peak. This was a result of methionine oxidation to the sulfoxide.

E. Methods of Analysis

Figure 5:
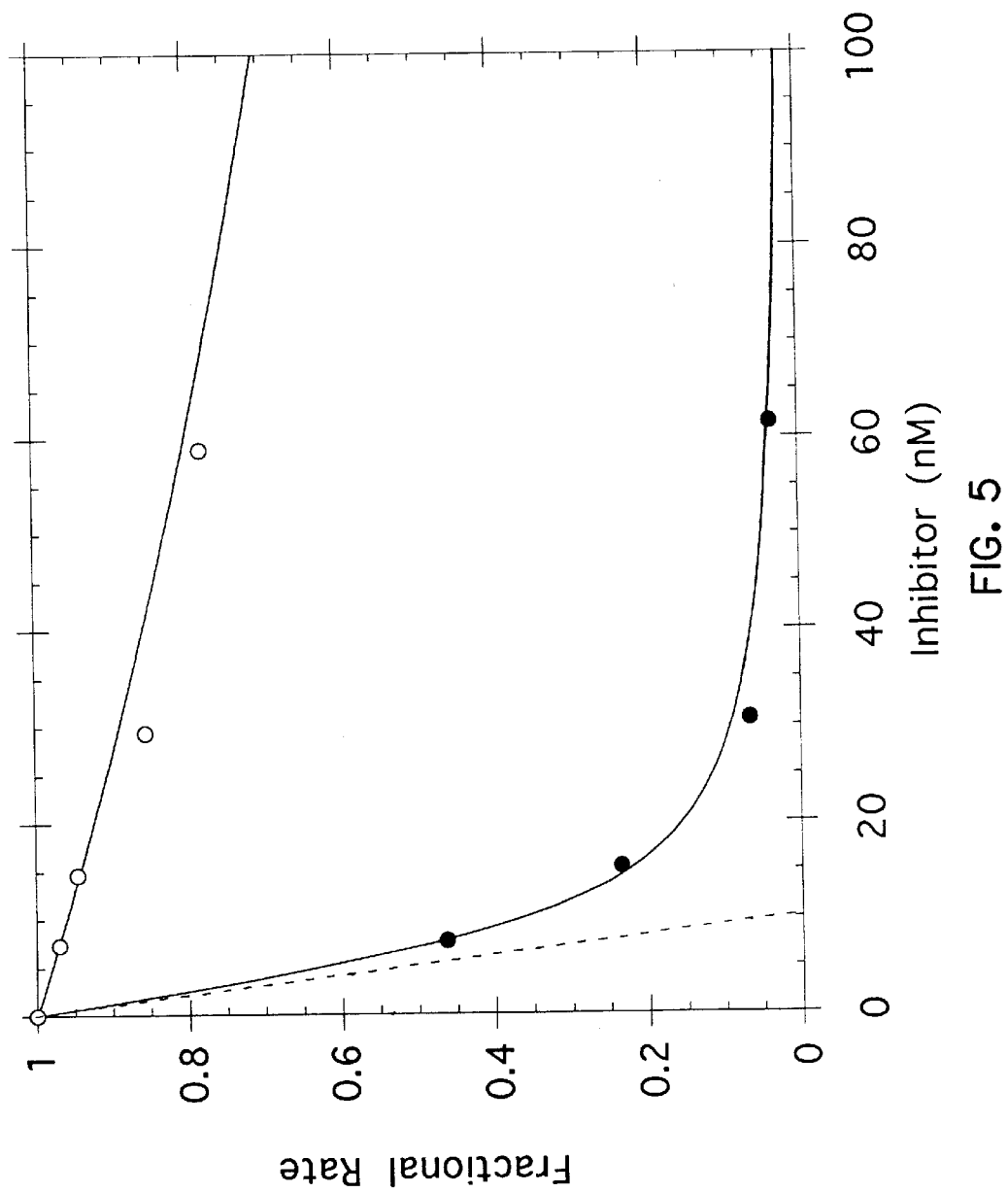
FIG. 5. Determination of the Apparent Equilibrium Dissociation Constants of TF7I-C and APPI with TF-FVIIa. The inhibitory activity is expressed as the fractional activity (inhibited rate/uninhibited rate) at varying inhibitor concentrations. For this determination, the FVIIa and TF$_{1-243}$ concentrations were 10 nM and 50 nM, respectively. The apparent equilibrium dissociation constants were determined by nonlinear regression analysis of the data using equation 1 and yielded $K_i^*$ values of 2.1 nM for TF7I-C (●) and 300 nM for APPI (○). The lines represent best fits of the data to equation 1 for the calculated $K_i^*$. The data is representative of nine independent determinations for TF7I-C and seven for APPI. The fractional activity for 1:1 stoichiometric inhibition is represented by a dashed line.

Apparent equilibrium dissociation constants ($K_i^*$) were determined using methods derived for tight-binding inhibitors (Bieth, J., *Proteinase Inhibitors* 463–469 [1974]; Williams, J. W. and Morrison, J. F., *Methods Enzymol* 63:437–467 [1979]), assuming enzyme and inhibitor form a reversible complex with a 1:1 stoichiometry as has been observed for the interaction of Kunitz domains with serine proteases (Bode, W. and R. Huber, *Eur. J. Biochem.* 204:433–451 [1992; Laskowski, M., Jr. and I. Kato, *Annu. Rev. Biochem.* 49:593–626 [1980]). The data were fit by nonlinear regression analysis to Equation 1:

$$V_i/V_o = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

where $V_i/V_o$ is the fractional activity (steady-state inhibited rate divided by the uninhibited rate), $[E_o]$ is the total FVIIa active site concentration, and $[I_o]$ is the total inhibitor concentration. Variants were assayed for their binding affinity to TF-FVIIa and those with $K_i$ values ranging from ca. 1–500 nM are shown in FIG. 4. The inhibition of TF-FVIIa by TF7I-C and APPI under equilibrium conditions is shown in FIG. 5; apparent $K_i^*$ values of 1.9±4 nM and 301±44 nM were calculated for TF7I-C and APPI with TF-FVIIa, respectively (FIG. 4).

By measuring apparent $K_i^*$ values with other relevant serine proteases found in human plasma, the relative specificities of wild type APPI, TF7I-C, and other mutant inhibitors were determined. To aliquots of serial diluted inhibitor, either activated protein C, thrombin, FXa, FXIa, FXIIa, plasma kallikrein or plasmin were added. After incubation and addition of the appropriate substrate, plots of fractional activity versus inhibitor concentration were generated as described in Example 3. Apparent equilibrium dissociation constants ($K_i^*$) were calculated from equation (1) and are reported in FIG. 4. APPI was a potent inhibitor of FXIa, in good agreement with previously reported results (Wagner, S. L. et al., *Biochem. Biophys. Res. Commun.* 186:1138–1145 [1992]) and a moderate inhibitor of TF-FVIIa, plasmin, and plasma kallikrein; the $K_i^*$ for activated protein C, thrombin, FXa, or FXIIa was >10 μM. In addition to potently inhibiting TF-FVIIa, TF7I-C is also a potent inhibitor of FXIa and plasma kallikrein and a moderate inhibitor of plasmin (FIG. 4). The $K_i^*$ for FXa=90 nM and was >10 μM for activated protein C, thrombin, or FXIIa. Other inhibitors were more specific inhibitors of TF-FVIIa with respect to FXIa, plasma kallikrein, or plasmin (FIG. 4).

Figure 6:
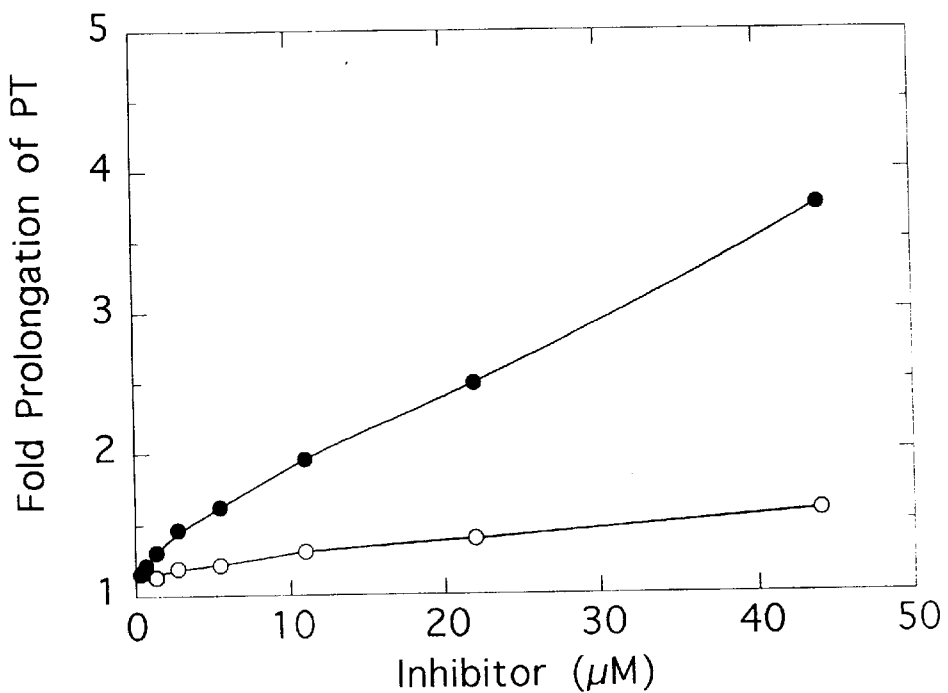
FIG. 6. Prolongation of clotting time in the PT assay in normal human plasma. The concentration of TF7I-C (●) and APPI (○) are plotted vs. the fold prolongation of clotting time upon initiation by TF membranes. The uninhibited clotting time was 30 sec.
Figure 7:
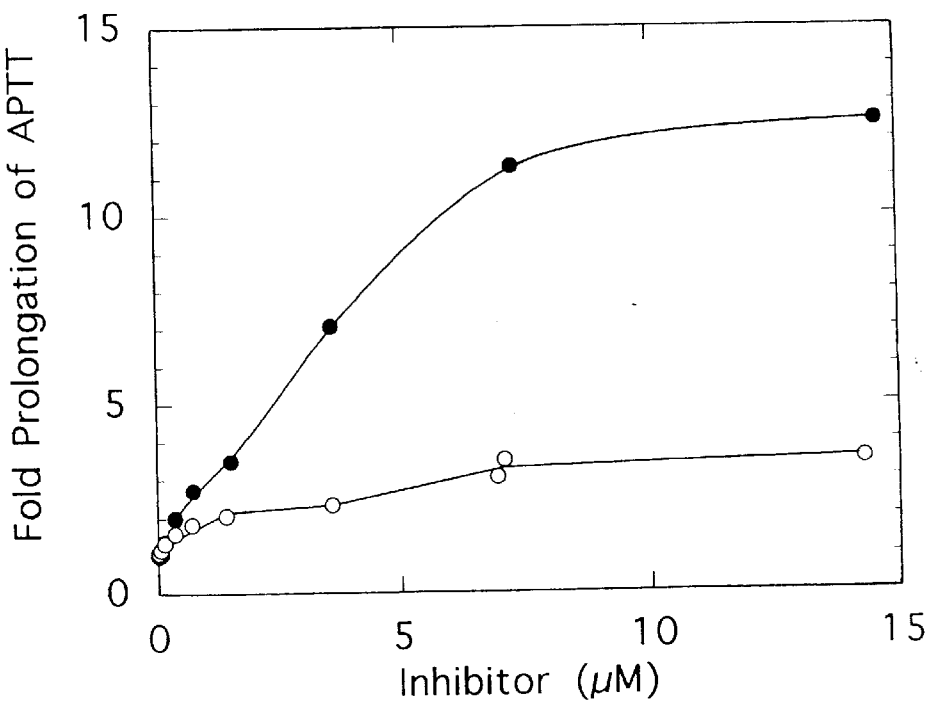
FIG. 7. Prolongation of clotting time in the APTT assay in normal human plasma. The concentration of TF7I-C (●) and APPI (○) are plotted vs. the fold prolongation of clotting time upon initiation by ellagic acid. The uninhibited clotting time was 31 sec.

Based on a tissue factor initiated prothrombin time (PT) assay described in Example 4, both TF7I-C and APPI prolonged the clotting time in a concentration dependent manner (FIG. 6). This is consistent with the ability of these inhibitors to prevent FX activation through inhibition of the TF-FVIIa complex. In this assay TF7I-C prolonged the clotting time 3.5-fold at ca. 40 μM, whereas the same concentration of APPI resulted in only a 1.5-fold increase in the clotting time. TF7I-C also showed concentration dependent inhibition of the surface mediated contact activation pathway, as measured by the activated partial thromboplastin time assay (APTT) described in Example 4, a greater than 10-fold prolongation of the clotting time at ca. 7 μM was observed (FIG. 7). APPI was somewhat less potent in the APTT relative to TF7I-C, having a clotting time of ca. 3-fold at the same concentration.

F. Pharmaceutical Compositions

Dosage formulations of the compounds of the present invention to be used for therapeutic applications must be sterile. Sterility is readily accomplished by filtration through sterile filtration membranes such as 0.2μ membranes. Protein formulations ordinarily will be stored in lyophilized form or as an aqueous solution. The pH of the protein preparations typically will be between about 3 and 11, more preferably from about 5 to 9, and most preferably from about 7 to 8. The preferred route of administration is by hypodermic needle.

Therapeutic protein formulations are generally placed into a container having a sterile access port, for example, an intravenous solution bag or vial having a stopper pierceable by a hypodermic injection needle.

Therapeutically effective dosages may be determined by either in vitro (see assays above) or in vivo methods. Based upon such assay techniques, a therapeutically effective dosage range may be determined. The range of therapeutically effective dosages will naturally be affected by the route of administration. For injection by hypodermic needle, it may be assumed that the dosage is delivered into the body's fluids. For other routes of administration, the adsorption efficiency must be individually determined for APPI variants by methods well-known in pharmacology.

The range of therapeutic dosages may range from about 0.001 nM to about 1.0 mM, more preferably from about 0.1 nM to about 100 μM, and most preferably from about 1.0 nM to about 50 μM.

A typical formulation of APPI variants as a pharmaceutical composition contains from about 0.5 to 500 mg of a compound or mixture of compounds as either the free acid or base form or as a pharmaceutically acceptable salt. These compounds or mixtures are then compounded with a physiologically acceptable vehicle, carrier, excipient, binder, preservative, or stabilizer, etc., as called for by accepted pharmaceutical practice. The amount of active ingredient in these compositions is such that a suitable dosage in the range indicated is obtained.

Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

EXAMPLES

Materials

Human Factor VIIa, Factor Xa, Factor XIa, activated protein C and thrombin were purchased from Haematologic Technologies Inc. (Essex Jct., Vt.). Human plasma kallikrein and Factor XIIa were purchased from Enzyme Research Laboratories, Inc. (South Bend, Ind.). Recombinant human tissue factor$_{1-243}$ (TF$_{1-243}$) was produced in $E.$ $coli$ and purified as previously described (Paborsky, L. R. et al., Biochemistry 28:8072–8077 [1989]; Paborsky, L. R. et al.,$J.$ $Biol.$ $Chem.$ 266:21911–21916 [1991]). Bovine trypsin, 4-methylumbelliferyl p-guanidinobenzoate and CHAPS were purchased from Sigma Chemicals, Inc. Bovine serum albumin (BSA), Fraction V was obtained from Calbiochem (La Jolla, Calif.). N$^{\alpha}$-Benzoyl-L-arginine-p-nitroanilide was purchased from Bachem California (Torrance, Calif.). Human plasmin, S-2302, S-2251 and S-2366 were purchased from Kabi Vitrum (Sweden) and Spectrozyme fXa was purchased from American Diagnostica (Greenwich, Conn.). Affigel-10 was obtained from Bio-Rad Laboratories (Richmond, Calif.). All other reagents were obtained were of the highest grade commercially available.

Example 1

Plasmid Construction and Mutagenesis

The plasmid pSAlzl was constructed by inserting a synthetic gene encoding the APPI sequence into an appropriate expression vector for secretion of APPI into the periplasm and media. The pSAlzl vector contained the alkaline phosphatase promoter, stII secretion signal, the APPI gene, the fl and colEl origins of replication, and the ampicillin resistance gene as described by Castro et al. (Castro, M. et al., FEBS Lett. 267:207–212 [1990]). The construction of APPI mutants using the pSAlzl vector was accomplished using site-directed oligonucleotide mutagenesis in as previously described (Kunkel, T. A. et al., Methods Enzymol. 204:125–139 [1991]); selected clones were analyzed by dideoxy sequence analysis (Sanger, F. et al., Proc Natl Acad Sci U.S.A. 74:5463–5467 [1977]).

Example 2

Inhibitor Expression, Purification, and Characterization

Phagemids encoding either APPI or the selected mutants were transformed into $E.$ $coli$ strain 27C7, a derivative of $E.$ $coli$ W3110, for expression of the Kunitz domain inhibitors. Overnight saturated cultures were inoculated (1%) into 250 ml of low phosphate minimal media (Chang, C. N. et al., Gene 55:189–196 [1987]) containing 50 μg/ml ampicillin and grown for 20 h at 37° C. Inhibitors were secreted into the periplasm by virtue of the stII signal sequence and eventually leaked into the media. Cells and debris were removed by centrifugation (8000×g, 10 min); the supernatant was adjusted to pH 7.5–8.5 with 1M NaOH and then loaded onto a 1 ml trypsin-Affigel 10 affinity column which was prepared according to the manufacturer's recommendations. The column was washed with 100 mM Tris pH 8, 100 mM NaCl, and 20 nM CaCl$_2$ and inhibitors were eluted with 4 ml of 10 mM HCl, 0.5M KCl. The inhibitors were further purified using C18 reverse phase HPLC (250×4.6 mm, VYDAC); they were loaded in 0.1% trifluoroacetic acid and eluted with a CH$_3$CN gradient from 5 to 40% at 1 ml/min. Elution profiles were monitored at both A$_{214}$ and A$_{280}$. A single well resolved peak was detected for each inhibitor between 30 to 35% CH$_3$CN. Inhibitor sequences were verified for the proper mass using a Sciex API 3 mass spectrometer equipped with an articulated electrospray source for mass analysis. Multiply charged ions of horse myoglobin (MW=16,951 Da) were used for instrument calibration.

Example 3

Determination of Equilibrium Dissociation Constants

Enzyme inhibition assays were conducted in a microtiter format and absorbance changes were monitored on an SLT EAR340AT plate reader controlled by a Macintosh SE computer equipped with Biometallics DeltaSoftII software. Nonlinear regression analysis was carried out using Kaleida-Graph v3.01 (Synergy Software).

Inhibitor stocks were diluted in the range of 5–2000 nM; concentrations were accurately determined by titration with trypsin that had been active site-titrated using 4-methylumbelliferyl p-guanidinobenzoate (Jameson, G. W. et al., *Biochem. J.* 131:107–117 [1973]). After a 1 h incubation of 80 nM trypsin plus an aliquot of diluted inhibitor in 50 mM Tris, pH 8.0, 100 mM NaCl, 10 mM $CaCl_2$, and 0.05% Triton X-100 at room temperature, 20 µl of 5 mM $N^\alpha$-benzoyl-L-arginine-p-nitroanilide was added to a total volume of 150 µl. The change in absorbance at 405 nm was then monitored. The concentrations determined assumed a 1:1 stoichiometry of inhibitor with trypsin.

Assays to test the activity of APPI, TF7I-C, and other mutants against coagulation proteases were conducted using the following format. Aliquots (25 µL) from each well of a microtiter plate containing the serially diluted inhibitors were transferred into new microtiter plates, each containing a different protease (100 µL) in the appropriate buffer. The proteases tested (protease concentration, buffer, substrate) were FVIIa (10 nM, Buffer A, 0.7 mM S2366), FXIa (1.0 nM, Buffer B containing 1 mg/ml BSA, 0.7 mM S2366), plasma kallikrein (3.5 nM, Buffer B, 0.5 mM S2302), and plasmin (15 nM, Buffer B, 1 mM S2251). Buffer A contains 50 mM Tris, pH 7.5, 100 mM NaCl, 10 mM $CaCl_2$, 0.5% BSA, 60 nM $TF_{1-243}$, and 1 mM CHAPS (Sigma). Buffer B contains 50 mM Tris, pH 7.5, 100 mM NaCl, 2 mM $CaCl_2$ and 0.005% Triton X-100.

After incubation of the substrate/inhibitor mixes at room temperature for 1–3 h, the appropriate substrate (20 µL) was added, and the absorbance at 405 nm was monitored. Controls lacking inhibitor and enzyme were assayed to measure the uninhibited and substrate hydrolysis rates, respectively. Plots of the fractional rate versus inhibitor concentration were fit by nonlinear regression analysis to equation 1 and apparent equilibrium dissociation constants ($K_i^*$) were determined. The concentrations of FXa, FXIIa, and kallikrein were active site titrated with a quantitated sample of ecotin, a reversible tight-binding inhibitor of these enzymes from *E. coli*, which was overexpressed and purified as previously described (U.S. patent application Ser. No. 08/121004, filed Sep. 14, 1993). The concentrations of FVIIa, FXIa, and kallikrein were active site titrated using a quantitated sample of TF7I-C. Both TF7I-C and ecotin were quantitated using active site titrated trypsin. The concentrations of FVIIa, FXa, FXIa, FXIIa and kallikrein agreed well (±10%) with the manufacturers' specifications (data not shown). The concentrations of activated protein C, thrombin and plasmin were based upon those of the supplier.

Results

The apparent $K_i^*$ values of wild type APPI, TF7I-C, as well as twenty-nine other mutant inhibitors for TF-FVIIa, and in some cases FXIa, Kallikrein, and Plasmin were determined. The amino acid sequences of APPI, TF7I-C and the other mutant inhibitors are described in FIG. 4. The sequences of the mutant inhibitors I-18, I-49, I-14, I-16, II-4, II-3, II-6, III-27, III-30, TF7I-VY, TF7I-LY, TF7I-WY, TF7I-PG, IV-47C, IV-54C, IV-31B, IV-49C, IV-50C, IV-57C, IV51C, IV-35B, IV-58C, IV-48C, IV-46C, IV-55C, IV-32B, IV-36B, IV-40B and 53b as well as TF7I-C are all based on the wild type APPI sequence which is represented by:

$R_1$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$R_2$-$Xaa_{34}$-$R_3$-$Xaa_{38}$-$Xaa_{39}$-$R_4$

In each case $R_1$ has the sequence:
Val-Arg-Glu-Val-Cys-Ser-Glu-Gln-Ala-Glu (SEQ ID NO: 6)

$R_2$ has the sequence:
Arg-Trp-Tyr-Phe-Asp-Val-Thr-Glu-Gly-Lys-Cys-Ala-Pro-Phe (SEQ ID NO: 14)

$R_3$ has the sequence:
Tyr-Gly-Gly; and $R_4$ has the sequence:
Gly-Asn-Arg-Asn-Asn-Phe-Asp-Thr-Glu-Glu-Tyr-Cys-Ala-Ala-Val-Cys-Gly-Ser-Ala (SEQ ID NO: 23) or
Gly-Asn-Arg-Asn-Asn-Phe-Asp-Thr-Glu-Glu-Tyr-Cys-Met-Ala-Val-Cys-Gly-Ser-Ala (SEQ ID NO: 24)

Therefore, the sequences of the mutant inhibitors tested in this Example are:

I-18 $R_1$-Pro-Gly-Val-Cys-Arg-Ala-Leu-Ile-Leu-$R_2$-Phe-$R_3$-Cys-Gly-$R_4$ (SEQ ID NO: 43)

I-49 $R_1$-Pro-Gly-Trp-Cys-Arg-Ala-Leu-Ile-Lue-$R_2$-Phe-$R_3$-Cys-Gly-$R_4$ (SEQ ID NO: 44)

I-14 $R_1$-Pro-Gly-Phe-Cys-Arg-Ala-Leu-Ile-Leu-$R_2$-Phe-$R_3$-Cys-Gly-$R_4$ (SEQ ID NO: 45)

I-16 $R_1$-Gly-Gly-Trp-Cys-Arg-Ala-Leu-Ile-Leu-$R_2$-Phe-$R_3$-Cys-Gly-$R_4$ (SEQ ID NO: 46)

where $R_4$ is the sequence identified by SEQ ID NO: 24, and

II-4 $R_1$-Pro-Gly-Pro-Cys-Arg-Ala-Met-Ile-Ser-$R_2$-Phe-$R_3$-Cys-Tyr-$R_4$ (SEQ ID NO: 47)

II-3 $R_1$-Pro-Gly-Trp-Cys-Arg-Ala-Met-Ile-Ser-$R_2$-Ile-$R_3$-Cys-Gly-$R_4$ (SEQ ID NO: 48)

II-6 $R_1$-Pro-Gly-Pro-Cys-Lys-Ala-Met-Ile-Ser-$R_2$-Ile-$R_3$-Cys-Trp-$R_4$ (SEQ ID NO: 49)

III-27 $R_1$-Thr-Gly-Pro-Cys-Arg-Ala-Leu-Ile-Ser-$R_2$-Trp-$R_3$-Cys-Gly-$R_4$ (SEQ ID NO: 50)

III-30 $R_1$-Thr-Gly-Pro-Cys-Arg-Ala-Leu-Ile-Ser-$R_2$-Tyr-$R_3$-Cys-Gly-$R_4$ (SEQ ID NO: 51)

TF7I-VY $R_1$-Pro-Gly-Val-Cys -Arg-Ala-Leu-Ile-Leu-$R_2$-Phe-$R_3$ -Cys -Tyr-$R_4$ (SEQ ID NO: 52)

TF7I-LY $R_1$-Pro-Gly-Leu-Cys-Arg-Ala-Leu-Ile-Leu-$R_2$-Phe-$R_3$-Cys-Tyr-$R_4$ (SEQ ID NO: 53)

TF7I-WY $R_1$-Pro-Gly-Trp-Cys-Arg-Ala-Leu-Ile-Leu-$R_2$-Phe-$R_3$-Cys-Tyr-$R_4$ (SEQ ID NO: 54)

TF7I-PG $R_1$-Pro-Gly-Pro-Cys -Arg-Ala-Leu-Ile-Leu-$R_2$-Phe-$R_3$ -Cys-Gly-$R_4$ (SEQ ID NO: 55)

IV-47C $R_1$-Pro-Gly-Pro-Cys-Arg-Ala-Met-Met-Lys-$R_2$-Ile-$R_3$-Cys-His -$R_4$ (SEQ ID NO: 56)

IV-54C $R_1$-Pro-Gly-Pro-Cys-Arg-Ala-Leu-Met-Lys-$R_2$-Val-$R_3$-Cys-Tyr-$R_4$ (SEQ ID NO: 57)

IV-31B $R_1$-Pro-Gly-Pro-Cys-Arg-Ala-Leu-Met-Lys-$R_2$-Val-$R_3$-Cys-Phe-$R_4$ (SEQ ID NO: 58)

IV-49C $R_1$-Pro-Gly-Pro-Cys-Arg-Ala-Met-Met-Lys-$R_2$-Ile-$R_3$-Cys-Tyr-$R_4$ (SEQ ID NO: 59)

IV-50C $R_1$-Pro-Gly-Pro-Cys -Arg-Ala-Met-Tyr-Lys-$R_2$-Ile-$R_3$-Cys-Tyr-$R_4$ (SEQ ID NO: 60)

IV-57C $R_1$-Pro-Gly-Val-Cys-Arg-Ala-Met-Met-Lys-$R_2$-Ile-$R_3$-Cys-Gly-$R_4$ (SEQ ID NO: 61)

IV-51C $R_1$-Pro-Gly-Pro-Cys-Lys-Ala-Leu-Met-Arg-$R_2$-Tyr-$R_3$-Cys-Tyr-$R_4$ (SEQ ID NO: 62)

IV-35B  $R_1$-Pro-Gly-Pro-Cys-Lys-Ala-Ile-Met-Lys-$R_2$-Ile-$R_3$-Cys-His-$R_4$ (SEQ ID NO: 63)

IV-58C  $R_1$-Pro-Gly-Pro-Cys-Lys-Ala-Leu-Met-Lys-$R_2$-Tyr-$R_3$-Cys-His-$R_4$ (SEQ ID NO: 64)

IV-48C  $R_1$-Pro-Gly-Pro-Cys-Lys-Ala-Leu-Met-Lys-$R_2$-Trp-$R_3$-Cys-Trp-$R_4$ (SEQ ID NO: 65)

IV-46C  $R_1$-Pro-Gly-Pro-Cys-Lys-Ala-Met-Ile-Lys-$R_2$-Leu-$R_3$-Cys-Tyr-$R_4$ (SEQ ID NO: 66)

IV-55C  $R_1$-Pro-Gly-Pro-Cys-Lys-Ala-Leu-Met-Lys-$R_2$-Phe-$R_3$-Cys-Tyr-$R_4$ (SEQ ID NO: 67)

IV-32B  $R_1$-Pro-Gly-Pro-Cys-Lys-Ala-Leu-Met-Lys-$R_2$-Tyr-$R_3$-Cys-Tyr-$R_4$ (SEQ ID NO: 68)

IV-36B  $R_1$-Pro-Gly-Pro-Cys-Lys-Ala-Leu-Met-Lys-$R_2$-Val-$R_3$-Cys-Tyr-$R_4$ (SEQ ID NO: 69)

IV-40B  $R_1$-Pro-Gly-Ala-Cys-Lys-Ala-Met-Tyr-Lys-$R_2$-Ile-$R_3$-Cys-Gly-$R_4$ (SEQ ID NO: 70)

53b  $R_1$-Pro-Gly-Pro-Gly-Arg-Ala-Leu-Ile-Leu-$R_2$-Phe-$R_3$-Ala-Tyr-$R_4$ (SEQ ID NO: 71)

and TF71-IC  $R_1$-Pro-Gly-Pro-Cys-Arg-Ala-Leu-Ile-Leu-$R_2$-Phe-$R_3$-Cys-Tyr-$R_4$ (SEQ ID NO: 72)

where $R_4$ has the sequence identified by SEQ ID NO: 23.

The results of the $K_i^*$ determinations are presented in FIG. 4. In some cases the $K_i^*$ was determined for FXIa, Kallikrein, and Plasmin as well as TFF-VIIa. As demonstrated, the substitutions with the exception of II-6, III-27, III-30 and IV-40B, resulted in more potent inhibitors of TF-FVIIa than wild type APPI.

Example 4

Coagulation Assays

Clotting times for normal human plasma were performed using the ACL 300 Research Coagulation Analyzer. For the prothrombin time (PT) assays, the incubation time was set at 120 sec and acquisition time at 120 to 600 sec depending on the expected outcome of the assay. Membranes from 293 cells expressing full length TF (Paborsky, L. R. et al., Biochemistry 28:8072–8077 [1989]) were premixed with $CaCl_2$. The sample (plasma and inhibitor) and reagent ($CaCl_2$/TF) were automatically mixed together after a 2 min incubation at 37° C. The clotting time was determined by optical assessment. The total incubation time of inhibitor with plasma before addition of $CaCl_2$/TF was ca. 5 min. Final concentrations were 2 to 20 $\mu$M inhibitor, 3.7 nM TF (0.9 $\mu$g/ml by protein content), 22.5 mM $CaCl_2$, and 50% plasma in a total volume of 160 $\mu$L.

For the activated partial thromboplastin time (APTT) assays, the activation time was set at 120 sec and acquisition time at 300 to 600 sec depending on the expected outcome of the assay. Citrated normal human plasma and inhibitor were incubated together. The sample (plasma and inhibitor) and activator (Instrumentation Laboratories Ellagic acid/Phospholipid mix Test Reagent) were automatically pipetted and incubated together for 2 min at 37° C., then $CaCl_2$ was added and clotting time determined by means of optical assessment. The total incubation time of inhibitor with plasma was ca. 3 min before addition of activator, and 5 min before addition of $CaCl_2$. Final concentrations were 0.01 to 15 $\mu$M inhibitor, 15.3 $\mu$g protein/ml 293 cell membranes, 8.3 $\mu$M ellagic acid, 8.3 mM $CaCl_2$, and 33.3% plasma in a total volume of 162 $\mu$L.

Results

The results are presented in Table I below.

TABLE I

In Vitro Clotting Times in Human Plasma
(fold prolongation) for Selected Variants

| Inhibitor | PT | APTT |
| --- | --- | --- |
| APPI | 1.5 | 3.6 |
| TF7I-C | 3.5 | >7.0 |
| IV-32B | 1.4 | 1.3 |
| IV-49C | 2.5 | 2.0 |
| IV-54C | 2.1 | 2.2 |

The clotting time in the absence of any inhibitor for the PT was 30s and for the APTT was 31s. The fold prolongation is reported at a concentration of 40 $\mu$M inhibitor.

Example 5

Rabbit Deep Medial Injury Model

Male New Zealand white rabbits (~4 kg) were anesthetized to surgical anesthesia plane with an IM injection of Ketamine/Xylaxine. The rabbits were placed supine on a restraining board, warmed to 37° C., and the neck and inner thigh area shaved. Teflon catheters were replaced in a marginal ear vein and femoral artery for drug delivery and sample collection respectively. Prior to treatment, blood samples were collected for coagulation tests (APTT and PT). Bleeding time was assessed from a cut made in the cuticle portion of a hind limb nail. Incisions were made in the neck region and the entire left common carotid artery and its branches were surgically isolated. An ultrasonic flow probe (Transonics®) was placed on the common carotid approximately 5 cm caudal to the common-internal bifurcation. After blood flow reached a stable baseline, drugs (saline or test compounds) were delivered via the marginal ear vein. A deflated embolectomy catheter (Fogarty®, 3F) was then introduced into the lumen of the common via an incision in the lingual branch. Blood flow through the artery was stopped briefly while the catheter was introduced and loosely secured with 2-0 silk tie at the incision site. After the catheter was in place and secure, blood flow was restored. The deflated balloon was advanced to within 2 mm of the flow probe and inflated with saline until resistance of the vessel wall was felt. The catheter was pulled back with a steady motion to the first branch and then deflated. This procedure was repeated a total of six times for each experimental animal, after which the catheter was removed. The ballooning procedure, from first insertion to removal of the catheter took 3 to 5 minutes and resulted in an area of damage that was 1.5 to 2 cm in length. Over 40 minutes, blood samples were taken for APTT and PT measurements, cuticle bleeding times were assessed and blood flow through the carotid monitored. Duration of patency was defined as the total amount of time (maximum=40 minutes) that any measurable blood flow is detected in the artery. Patency rate refers to the percentage of animals tested who had carotid artery blood flow $\geq$5 minutes. At the end of the experiment the rabbit was euthanized and the carotid artery removed and opened. If any thrombus was present, it was removed, blotted and the weight recorded.

Results

TABLE II

Clotting Times in Rabbit Plasma
(Fold Increase over Baseline @40 μM* or 50 μM*)

|  | APTT | PT |
|---|---|---|
| APPI* | 4.9 | 1.4 |
| TF7I-C* | >10 | 6.9 |
| IV-32B+ | 4.4 | 1.2 |
| IV-49C+ | 6.9 | 4.4 |
| IV-54C+ | 5.4 | 3.5 |

Samples of rabbit plasma were assayed using an MLA 800 coagulometer and Dade reagents. Actin FS® was the activator in the APTT assay. Rabbit Thromboplastin with Ca++ was used for the PT assays; the rabbit thromboplastin was diluted two-fold. All mutant inhibitors tested prolonged clotting by at least one fold. TF7I-C showed the greatest inhibition of the surface mediated contact activation pathway, as measured by the activated partial thromboplastin time assay. A greater than 10 fold prolongation of the clotting time at 40 μM was observed.

TABLE III

In Vivo: Rabbit Deep Medial Injury Model

|  | Patency (%) | Patency (N) | Duration (Min.) | Clot (mgs) |
|---|---|---|---|---|
| Saline Control | 0 | 0/11 | 0 | 92.1 ± 6.6 |
| Heparin 1 | 67 | 6/9 | 23.3 ± 6.7 | 13.6 ± 4.7 |
| Heparin 2 | 100 | 10/10 | 35.2 ± 2.2 | 19.1 ± 8.5 |
| APPI | 40 | 2/5 | 13.4 ± 8.5 | 49.5 ± 18.2 |
| TF7I-C | 83 | 5/6 | 30.3 ± 6.7 | 19.4 ± 14.6 |
| IV-49C | 83 | 5/6 | 33.3 ± 6.7 | 19.7 ± 9.6 |

[Heparin was dosed as a 25 u/kg bolus followed by a continuous infusion of 1) 0.5 u/kg/min or 2) 1 u/kg/min. Other reagents were given as a 2 mg/kg IV bolus. With the exception of the patency data, values are expressed as means ±sem.]

Compared to the saline control, Heparin and the mutant APPI inhibitors TF7I-C and IV-49C significantly prolonged patency and reduced clot size for the time periods studied. For both TF7I-C and IV-49C the percentage of animals that remained patent for greater than or equal to 5 minutes was 83% compared to only 40% for the wild type APPI.

Table 3 below describes the results of the cuticle bleeding time assay at 10 minutes after dosing.

TABLE IV

Cuticle Bleeding Times (Fold Increase over Pre Dose)

|  | N | Fold Increase |
|---|---|---|
| Saline Control | 6 | 1.0 ± 0.1 |
| Heparin 1 | ND |  |
| Heparin 2 | 5 | 1.7 ± 0.4 |
| APPI | 4 | 2.2 ± 0.6 |
| TF7I-C | 4 | 0.7 ± 0.1 |
| IV-49C | 6 | 1.0 ± 1.0 |

As demonstrated by the results of the cuticle bleeding time assay, mutant APPI inhibitors such as TF7I-C and IV-49C may have improved safety profiles compared to current anticoagulant drugs such as Heparin. These two mutant inhibitors did not induce prolonged bleeding compared to the saline control after 10 minutes.

All references cited herein are expressly incorporated by reference.

---

What is claimed is:

1. A method of treating a mammal in which inhibiting Factor VIIa, is indicated comprising administering to the mammal a pharmaceutically effective amount of a pharmaceutical composition comprising a pharmaceutically acceptable excipient and a polypeptide comprising a Kunitz-type serine protease inhibitor domain having an equilibrium dissociation constant of less than 100 nM for tissue factor-Factor VIIa represented by Structural Formula (I):

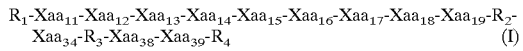

$R_1$-Xaa$_{11}$-Xaa$_{12}$-Xaa$_{13}$-Xaa$_{14}$-Xaa$_{15}$-Xaa$_{16}$-Xaa$_{17}$-Xaa$_{18}$-Xaa$_{19}$-$R_2$-Xaa$_{34}$-$R_3$-Xaa$_{38}$-Xaa$_{39}$-$R_4$     (I)

where $R_1$ is a peptide having from 5 to 10 amino acid residues wherein at least one residue is Cys;

$R_2$ is a peptide having 14 amino acid residues wherein at least one residue is Cys;

$R_3$ is a tripeptide;

$R_4$ is a peptide having from 12 to 19 amino acid residues wherein at least one residue is Cys;

Xaa$_{11}$ is selected from the group Pro, Arg, Ala, Glu, Gly, and Thr;

Xaa$_{12}$ is Gly;

Xaa$_{13}$ is selected from the group Pro, Leu, Trp, Val, Gly, Phe, His, Tyr, Ala, Ile, Glu, and Gln;

Xaa$_{14}$ is selected from Cys, Ala, Ser, Thr, and Gly;

Xaa$_{15}$ is selected from Met, Arg, and Lys;

Xaa$_{16}$ is selected from Gly and Ala;

Xaa$_{17}$ is selected from the group Met, Leu, Ile, Arg, Tyr, and Ser;

Xaa$_{18}$ is selected from the group Ile, His, Leu, Met, Tyr, and Phe;

Xaa$_{19}$ is selected from the group Leu, Arg, Ala, Lys, and Ile;

Xaa$_{34}$ is selected from the group Phe, Ile, Ser, Leu, Tyr, Trp, and Val;

Xaa$_{38}$ is selected from Cys, Ala, Ser, Thr, and Gly; and

Xaa$_{39}$ is selected from the group Tyr, Gly, Trp, His, and Phe; provided $R_1$ is not Xaa$_1$-Asp-Ile-Cys-Lys-Leu-Pro-Lys-Asp (SEQ ID NO: 1), where Xaa$_1$ is His or 1–5 amino acid residues; and Xaa$_{11}$ through Xaa$_{19}$ are not Pro-Gly-Phe-Ala-Lys-Ala-Ile-Ile-Arg (SEQ ID NO: 2);

Thr-Gly-Leu-Cys-Lys-Ala-Tyr-Ile-Arg (SEQ ID NO: 3);

Thr-Gly-Leu-Cys-Lys-Ala-Arg-Ile-Arg (SEQ ID NO: 4); and

Ala-Gly-Ala-Ala-Lys-Ala-Leu-Leu-Ala (SEQ ID NO: 5).

2. The method of claim 1 wherein $R_1$ is a 10 amino acid peptide, $R_4$ is 19 amino acid peptide and amino acid residues 5, 14, 30, 38, 51 and 55 of the Kunitz-type domain are Cys.

3. The method of claim 2 wherein

Xaa$_{11}$ is Pro;

Xaa$_{12}$ is Gly;

Xaa$_{13}$ is selected from the group consisting of Pro, Trp, Val, and Leu;

Xaa$_{14}$ is Cys;

Xaa$_{15}$ is selected from the group consisting of Arg and Lys;

Xaa$_{16}$ is Ala;

Xaa$_{17}$ is selected from the group consisting of Leu, and Met;

Xaa$_{18}$ is selected from the group consisting of Met, and Ile;

Xaa$_{19}$ is selected from the group consisting of Lys, Arg and Leu;

Xaa$_{34}$ is selected from the group consisting of Phe, Val, Ile, Tyr;

Xaa$_{39}$ is selected from the group consisting of Tyr, Gly, and His.

4. The method of claim 3 wherein

Xaa$_{17}$ is Leu;

Xaa$_{18}$ is Met; and

Xaa$_{19}$ is selected from the group consisting of Lys and Arg.

5. The method of claim 4 where $R_1$ is Val-Arg-Glu-Val-Cys-Ser-Glu-Gln-Ala-Glu (SEQ ID NO: 6), $R_2$ is Arg-Trp-Try-Phe-Asp-Val-Thr-Glu-Gly-Lys-Cys-Ala-Pro-Phe (SEQ ID NO: 14) and $R_4$ is Gly-Asn-Arg-Asn-Asn-Phe-Asp-Thr-Glu-Glu-Tyr-Cys-Ala-Ala-Val-Cys-Gly-Ser-Ala (SEQ ID NO: 23).

6. The method of claim 3 wherein

Xaa$_{17}$ is Leu;

Xaa$_{18}$ is Ile; and

Xaa$_{19}$ is Leu.

7. The method of 6 where $R_1$ is Val-Arg-Glu-Val-Cys-Ser-Glu-Gln-Ala-Glu (SEQ ID NO: 6), $R_2$ is Arg-Trp-Try-Phe-Asp-Val-Thr-Glu-Gly-Lys-Cys-Ala-Pro-Phe (SEQ ID NO: 14) and $R_4$ is Gly-Asn-Arg-Asn-Asn-Phe-Asp-Thr-Glu-Glu-Tyr-Cys-Ala-Ala-Val-Cys-Gly Ser-Ala (SEQ ID NO: 23).

8. The method of claim 7 wherein the polypeptide has the amino acid sequence of SEQ ID NO: 72.

9. A method for inhibiting thrombus formation in a mammal comprising administering to the mammal a pharmaceutically effective amount of a pharmaceutical composition comprising a pharmaceutically acceptable excipient and a polypeptide comprising a Kunitz-type serine protease inhibitor domain having an equilibrium dissociation constant of less than 100 nM for tissue factor-Factor VIIa represented by Structural Formula (I):

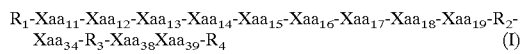

$$R_1\text{-}Xaa_{11}\text{-}Xaa_{12}\text{-}Xaa_{13}\text{-}Xaa_{14}\text{-}Xaa_{15}\text{-}Xaa_{16}\text{-}Xaa_{17}\text{-}Xaa_{18}\text{-}Xaa_{19}\text{-}R_2\text{-}Xaa_{34}\text{-}R_3\text{-}Xaa_{38}Xaa_{39}\text{-}R_4 \quad (I)$$

where $R_1$ is a peptide having from 5 to 10 amino acid residues wherein at least one residue is Cys;

$R_2$ is a peptide having 14 amino acid residues wherein at least one residue is Cys;

$R_3$ is a tripeptide;

$R_4$ is a peptide having from 12 to 19 amino acid residues wherein at least one residue is Cys;

$Xaa_{11}$ is selected from the group Pro, Arg, Ala, Glu, Gly, and Thr;

$Xaa_{12}$ is Gly;

$Xaa_{13}$ is selected from the group Pro, Leu, Trp, Val, Gly, Phe, His, Tyr, Ala, Ile, Glu, and Gln;

$Xaa_{14}$ is selected from Cys, Ala, Ser, Thr, and Gly;

$Xaa_{15}$ is selected from Met, Arg, and Lys;

$Xaa_{16}$ is selected from Gly and Ala;

$Xaa_{17}$ is selected from the group Met, Leu, Ile, Arg, Tyr, and Ser;

$Xaa_{18}$ is selected from the group Ile, His, Leu, Met, Tyr, and Phe;

$Xaa_{19}$ is selected from the group Leu, Arg, Ala, Lys, and Ile;

$Xaa_{34}$ is selected from the group Phe, Ile, Ser, Leu, Tyr, Trp, and Val;

$Xaa_{38}$ is selected from Cys, Ala, Ser, Thr, and Gly; and $Xaa_{39}$ is selected from the group Tyr, Gly, Trp, His, and Phe; provided $R_1$ is not $Xaa_1$-Asp-Ile-Cys-Lys-Leu-Pro-Lys-Asp (SEQ ID NO: 1), where $Xaa_1$ is His or 1–5 amino acid residues; and $Xaa_{11}$ through $Xaa_{19}$ are not
Pro-Gly-Phe-Ala-Lys-Ala-Ile-Ile-Arg (SEQ ID NO: 2);
Thr-Gly-Leu-Cys-Lys-Ala-Tyr-Ile-Arg (SEQ ID NO: 3);
Thr-Gly-Leu-Cys-Lys-Ala-Arg-Ile-Arg (SEQ ID NO: 4); and
Ala-Gly-Ala-Ala-Lys-Ala-Leu-Leu-Ala (SEQ ID NO: 5).

10. The method of claim 9 further comprising administrating the composition in combination with a thrombolytic agent.

11. The method of claim 9 further comprising administrating the composition in combination with an anticoagulant.

* * * * *

SEQUENCE LISTING ( 1 ) GENERAL INFORMATION:

( i i i ) NUMBER OF SEQUENCES: 72

( 2 ) INFORMATION FOR SEQ ID NO:1:

( i ) SEQUENCE CHARACTERISTICS:
        ( A ) LENGTH: 8 amino acids
        ( B ) TYPE: Amino Acid
        ( D ) TOPOLOGY: Linear ( x i ) SEQUENCE DESCRIPTION: SEQ ID NO:1:

Asp Ile Cys Lys Leu Pro Lys Asp
1               5               8

( 2 ) INFORMATION FOR SEQ ID NO:2:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:2:

Pro Gly Phe Ala Lys Ala Ile Ile Arg
1               5               9

( 2 ) INFORMATION FOR SEQ ID NO:3:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:3:

Thr Gly Leu Cys Lys Ala Tyr Ile Arg
1               5                 9

( 2 ) INFORMATION FOR SEQ ID NO:4:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:4:

Thr Gly Leu Cys Lys Ala Arg Ile Arg
1               5                 9

( 2 ) INFORMATION FOR SEQ ID NO:5:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:5:

Ala Gly Ala Ala Lys Ala Leu Leu Ala
1               5                 9

( 2 ) INFORMATION FOR SEQ ID NO:6:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:6:

Val Arg Glu Val Cys Ser Glu Gln Ala Glu
1               5                   10

( 2 ) INFORMATION FOR SEQ ID NO:7:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:7:

Met His Ser Phe Cys Ala Phe Lys Ala Asp
1               5                   10

( 2 ) INFORMATION FOR SEQ ID NO:8:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:8:

Lys Pro Asp Phe Cys Phe Leu Glu Glu Asp
1               5                   10

( 2 ) INFORMATION FOR SEQ ID NO:9:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:9:

```
Gly  Pro  Ser  Trp  Cys  Leu  Thr  Pro  Ala  Asp
 1                    5                         10
```

( 2 ) INFORMATION FOR SEQ ID NO:10:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:10:

```
Lys  Glu  Asp  Ser  Cys  Gln  Leu  Gly  Tyr  Ser
 1                    5                         10
```

( 2 ) INFORMATION FOR SEQ ID NO:11:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:11:

```
Thr  Val  Ala  Ala  Cys  Asn  Leu  Pro  Ile  Val
 1                    5                         10
```

( 2 ) INFORMATION FOR SEQ ID NO:12:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:12:

```
Leu  Pro  Asn  Val  Cys  Ala  Phe  Pro  Met  Glu
 1                    5                         10
```

( 2 ) INFORMATION FOR SEQ ID NO:13:

( i ) SEQUENCE CHARACTERISTICS:
        ( A ) LENGTH: 10 amino acids
        ( B ) TYPE: Amino Acid
        ( D ) TOPOLOGY: Linear ( x i ) SEQUENCE DESCRIPTION: SEQ ID NO:13:

```
Arg  Pro  Asp  Phe  Cys  Leu  Glu  Pro  Pro  Tyr
 1                    5                         10
```

( 2 ) INFORMATION FOR SEQ ID NO:14:

( i ) SEQUENCE CHARACTERISTICS:
        ( A ) LENGTH: 14 amino acids
        ( B ) TYPE: Amino Acid
        ( D ) TOPOLOGY: Linear ( x i ) SEQUENCE DESCRIPTION: SEQ ID NO:14:

```
Arg  Trp  Tyr  Phe  Asp  Val  Thr  Glu  Gly  Lys  Cys  Ala  Pro  Phe
 1                    5                         10                  14
```

( 2 ) INFORMATION FOR SEQ ID NO:15:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:15:

Arg Phe Phe Phe Asn Ile Phe Thr Arg Gln Cys Glu Glu Phe
1               5                   10                  14

( 2 ) INFORMATION FOR SEQ ID NO:16:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:16:

Arg Tyr Phe Tyr Asn Asn Gln Thr Lys Gln Cys Glu Arg Phe
1               5                   10                  14

( 2 ) INFORMATION FOR SEQ ID NO:17:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:17:

Arg Phe Tyr Tyr Asn Ser Val Ile Gly Lys Cys Arg Pro Phe
1               5                   10                  14

( 2 ) INFORMATION FOR SEQ ID NO:18:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:18:

Arg Tyr Phe Tyr Asn Gly Thr Ser Met Ala Cys Glu Thr Phe
1               5                   10                  14

( 2 ) INFORMATION FOR SEQ ID NO:19:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:19:

Leu Trp Ala Phe Asp Ala Val Lys Gly Lys Cys Val Leu Phe
1               5                   10                  14

( 2 ) INFORMATION FOR SEQ ID NO:20:

(  i  ) SEQUENCE CHARACTERISTICS:
    ( A ) LENGTH: 14 amino acids
    ( B ) TYPE: Amino Acid
    ( D ) TOPOLOGY: Linear ( x i ) SEQUENCE DESCRIPTION: SEQ ID NO:20:

Lys Trp Tyr Tyr Asp Pro Asn Thr Lys Ser Cys Ala Arg Phe
1               5                   10                  14

( 2 ) INFORMATION FOR SEQ ID NO:21:

(  i  ) SEQUENCE CHARACTERISTICS:
    ( A ) LENGTH: 14 amino acids (B) TYPE: Amino Acid
(D) TOPOLOGY: Linear (xi) SEQUENCE DESCRIPTION: SEQ ID NO:21:

Arg Trp Phe Phe Asn Phe Glu Thr Gly Glu Cys Glu Leu Phe
1               5                   10                  14

(2) INFORMATION FOR SEQ ID NO:22:

(i) SEQUENCE CHARACTERISTICS:
(A) LENGTH: 14 amino acids
(B) TYPE: Amino Acid
(D) TOPOLOGY: Linear (xi) SEQUENCE DESCRIPTION: SEQ ID NO:22:

Arg Tyr Phe Tyr Asn Ala Lys Ala Gly Leu Cys Gln Thr Phe
1               5                   10                  14

(2) INFORMATION FOR SEQ ID NO:23:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:23:

Gly Asn Arg Asn Asn Phe Asp Thr Glu Glu Tyr Cys Ala Ala Val
1               5                   10                      15

Cys Gly Ser Ala
            19

(2) INFORMATION FOR SEQ ID NO:24:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:24:

Gly Asn Arg Asn Asn Phe Asp Thr Glu Glu Tyr Cys Met Ala Val
1               5                   10                      15

Cys Gly Ser Ala
            19

(2) INFORMATION FOR SEQ ID NO:25:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:25:

Gly Asn Gln Asn Arg Phe Glu Ser Leu Glu Glu Cys Lys Lys Met
1               5                   10                      15

Cys Thr Arg Asp
            19

(2) INFORMATION FOR SEQ ID NO:26:

(i) SEQUENCE CHARACTERISTICS:
(A) LENGTH: 19 amino acids
(B) TYPE: Amino Acid
(D) TOPOLOGY: Linear (xi) SEQUENCE DESCRIPTION: SEQ ID NO:26:

Gly Asn Met Asn Asn Phe Glu Thr Leu Glu Glu Cys Lys Asn Ile

Cys Glu Asp Gly
             19

( 2 ) INFORMATION FOR SEQ ID NO:27:

( i ) SEQUENCE CHARACTERISTICS:
        ( A ) LENGTH: 19 amino acids
        ( B ) TYPE: Amino Acid
        ( D ) TOPOLOGY: Linear ( x i ) SEQUENCE DESCRIPTION: SEQ ID NO:27:

Gly Asn Glu Asn Asn Phe Thr Ser Lys Gln Glu Cys Leu Arg Ala
1               5                   10                  15
Cys Lys Lys Gly
             19

( 2 ) INFORMATION FOR SEQ ID NO:28:

( i ) SEQUENCE CHARACTERISTICS:
        ( A ) LENGTH: 19 amino acids
        ( B ) TYPE: Amino Acid
        ( D ) TOPOLOGY: Linear ( x i ) SEQUENCE DESCRIPTION: SEQ ID NO:28:

Gly Asn Gly Asn Asn Phe Val Thr Glu Lys Glu Cys Leu Gln Thr
1               5                   10                  15
Cys Arg Thr Val
             19

( 2 ) INFORMATION FOR SEQ ID NO:29:

( i ) SEQUENCE CHARACTERISTICS:
        ( A ) LENGTH: 19 amino acids
        ( B ) TYPE: Amino Acid
        ( D ) TOPOLOGY: Linear ( x i ) SEQUENCE DESCRIPTION: SEQ ID NO:29:

Gly Asn Gly Asn Lys Phe Tyr Ser Glu Lys Glu Cys Arg Glu Tyr
1               5                   10                  15
Cys Gly Val Pro
             19

( 2 ) INFORMATION FOR SEQ ID NO:30:

( i ) SEQUENCE CHARACTERISTICS:
        ( A ) LENGTH: 19 amino acids
        ( B ) TYPE: Amino Acid
        ( D ) TOPOLOGY: Linear ( x i ) SEQUENCE DESCRIPTION: SEQ ID NO:30:

Gly Asn Glu Asn Lys Phe Gly Ser Gln Lys Glu Cys Glu Lys Val
1               5                   10                  15
Cys Ala Pro Val
             19

( 2 ) INFORMATION FOR SEQ ID NO:31:

( i ) SEQUENCE CHARACTERISTICS:
        ( A ) LENGTH: 19 amino acids
        ( B ) TYPE: Amino Acid
        ( D ) TOPOLOGY: Linear ( x i ) SEQUENCE DESCRIPTION: SEQ ID NO:31:

Gly Asn Ser Asn Asn Phe Leu Arg Lys Glu Lys Cys Glu Lys Phe

```
                1               5                         10                        15

Cys   Lys   Phe   Thr
                            1 9
```

(2) INFORMATION FOR SEQ ID NO:32:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO:32:

```
        Ala   Lys   Arg   Asn   Asn   Phe   Lys   Ser   Ala   Glu   Asp   Cys   Met   Arg   Thr
         1                     5                         10                        15
        Cys   Gly   Gly   Ala
                            1 9
```

(2) INFORMATION FOR SEQ ID NO:33:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:33:

```
        Val   Arg   Glu   Val   Cys   Ser   Glu   Gln   Ala   Glu   Pro   Gly   Pro   Cys   Arg
         1                     5                         10                        15

Ala   Leu   Ile   Leu   Arg   Trp   Tyr   Phe   Asp   Val   Thr   Glu   Gly   Lys   Cys
                           2 0                        2 5                        3 0

Ala   Pro   Phe   Phe   Tyr   Gly   Gly   Cys   Tyr   Gly   Asn   Arg   Asn   Asn   Phe
                           3 5                        4 0                        4 5

Asp   Thr   Glu   Glu   Tyr   Cys   Ala   Ala   Val   Cys   Gly   Ser   Ala
                           5 0                        5 5                   5 8
```

(2) INFORMATION FOR SEQ ID NO:34:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:34:

```
        Val   Arg   Glu   Val   Cys   Ser   Glu   Gln   Ala   Glu   Thr   Gly   Pro   Cys   Arg
         1                     5                         10                        15

Ala   Met   Ile   Ser   Arg   Trp   Tyr   Phe   Asp   Val   Thr   Glu   Gly   Lys   Cys
                           2 0                        2 5                        3 0

Ala   Pro   Phe   Phe   Tyr   Gly   Gly   Cys   Gly   Gly   Asn   Arg   Asn   Asn   Phe
                           3 5                        4 0                        4 5

Asp   Thr   Glu   Glu   Tyr   Cys   Met   Ala   Val   Cys   Gly   Ser   Ala
                           5 0                        5 5                   5 8
```

(2) INFORMATION FOR SEQ ID NO:35:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:35:

```
        Met   His   Ser   Phe   Cys   Ala   Phe   Lys   Ala   Asp   Asp   Gly   Pro   Cys   Lys
         1                     5                         10                        15

Ala   Ile   Met   Lys   Arg   Phe   Phe   Phe   Asn   Ile   Phe   Thr   Arg   Gln   Cys
                           2 0                        2 5                        3 0
```

Glu Glu Phe Ile Tyr Gly Gly Cys Glu Gly Asn Gln Asn Arg Phe
                35                      40                      45
Glu Ser Leu Glu Glu Cys Lys Lys Met Cys Thr Arg Asp
                50                      55          58

(2) INFORMATION FOR SEQ ID NO:36:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:36:

Lys Pro Asp Phe Cys Phe Leu Glu Glu Asp Pro Gly Ile Cys Arg
1               5                       10                      15
Gly Tyr Ile Thr Arg Tyr Phe Tyr Asn Asn Gln Thr Lys Gln Cys
                20                      25                      30
Glu Arg Phe Lys Tyr Gly Gly Cys Leu Gly Asn Met Asn Asn Phe
                35                      40                      45
Glu Thr Leu Glu Glu Cys Lys Asn Ile Cys Glu Asp Gly
                50                      55          58

(2) INFORMATION FOR SEQ ID NO:37:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:37:

Gly Pro Ser Trp Cys Leu Thr Pro Ala Asp Arg Gly Leu Cys Arg
1               5                       10                      15
Ala Asn Glu Asn Arg Phe Tyr Tyr Asn Ser Val Ile Gly Lys Cys
                20                      25                      30
Arg Pro Phe Lys Tyr Ser Gly Cys Gly Gly Asn Glu Asn Asn Phe
                35                      40                      45
Thr Ser Lys Gln Glu Cys Leu Arg Ala Cys Lys Lys Gly
                50                      55          58

(2) INFORMATION FOR SEQ ID NO:38:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:38:

Lys Glu Asp Ser Cys Gln Leu Gly Tyr Ser Ala Gly Pro Cys Met
1               5                       10                      15
Gly Met Thr Ser Arg Tyr Phe Tyr Asn Gly Thr Ser Met Ala Cys
                20                      25                      30
Glu Thr Phe Gln Tyr Gly Gly Cys Met Gly Asn Gly Asn Asn Phe
                35                      40                      45
Val Thr Glu Lys Glu Cys Leu Gln Thr Cys Arg Thr Val
                50                      55          58

(2) INFORMATION FOR SEQ ID NO:39:

(i) SEQUENCE CHARACTERISTICS:
        (A) LENGTH: 58 amino acids
        (B) TYPE: Amino Acid
        (D) TOPOLOGY: Linear ( x i ) SEQUENCE DESCRIPTION: SEQ ID NO:39:

```
Thr  Val  Ala  Ala  Cys  Asn  Leu  Pro  Ile  Val  Arg  Gly  Pro  Cys  Arg
 1                   5                        10                       15

Ala  Phe  Ile  Gln  Leu  Trp  Ala  Phe  Asp  Ala  Val  Lys  Gly  Lys  Cys
                    20                        25                       30

Val  Leu  Phe  Pro  Tyr  Gly  Gly  Cys  Gln  Gly  Asn  Gly  Asn  Lys  Phe
                    35                        40                       45

Tyr  Ser  Glu  Lys  Glu  Cys  Arg  Glu  Tyr  Cys  Gly  Val  Pro
                    50                        55             58
```

( 2 ) INFORMATION FOR SEQ ID NO:40:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:40:

```
Glu  Thr  Asp  Ile  Cys  Lys  Leu  Pro  Lys  Asp  Glu  Gly  Thr  Cys  Arg
 1                   5                        10                       15

Asp  Phe  Ile  Leu  Lys  Trp  Tyr  Tyr  Asp  Pro  Asn  Thr  Lys  Ser  Cys
                    20                        25                       30

Ala  Arg  Phe  Trp  Tyr  Gly  Gly  Cys  Gly  Gly  Asn  Glu  Asn  Lys  Phe
                    35                        40                       45

Gly  Ser  Gln  Lys  Glu  Cys  Glu  Lys  Val  Cys  Ala  Pro  Val
                    50                        55             58
```

( 2 ) INFORMATION FOR SEQ ID NO:41:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:41:

```
Leu  Pro  Asn  Val  Cys  Ala  Phe  Pro  Met  Glu  Lys  Gly  Pro  Cys  Gln
 1                   5                        10                       15

Thr  Tyr  Met  Thr  Arg  Trp  Phe  Phe  Asn  Phe  Glu  Thr  Gly  Glu  Cys
                    20                        25                       30

Glu  Leu  Phe  Ala  Tyr  Gly  Gly  Cys  Gly  Gly  Asn  Ser  Asn  Asn  Phe
                    35                        40                       45

Leu  Arg  Lys  Glu  Lys  Cys  Glu  Lys  Phe  Cys  Lys  Phe  Thr
                    50                        55             58
```

( 2 ) INFORMATION FOR SEQ ID NO:42:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:42:

```
Arg  Pro  Asp  Phe  Cys  Leu  Glu  Pro  Pro  Tyr  Thr  Gly  Pro  Cys  Lys
 1                   5                        10                       15

Ala  Arg  Ile  Ile  Arg  Tyr  Phe  Tyr  Asn  Ala  Lys  Ala  Gly  Leu  Cys
                    20                        25                       30

Gln  Thr  Phe  Val  Tyr  Gly  Gly  Cys  Arg  Ala  Lys  Arg  Asn  Asn  Phe
                    35                        40                       45

Lys  Ser  Ala  Glu  Asp  Cys  Met  Arg  Thr  Cys  Gly  Gly  Ala
                    50                        55             58
```

( 2 ) INFORMATION FOR SEQ ID NO:43:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:43:

```
Val  Arg  Glu  Val  Cys  Ser  Glu  Gln  Ala  Glu  Pro  Gly  Val  Cys  Arg
 1              5                        10                            15

Ala  Leu  Ile  Leu  Arg  Trp  Tyr  Phe  Asp  Val  Thr  Glu  Gly  Lys  Cys
              20                        25                            30

Ala  Pro  Phe  Phe  Tyr  Gly  Gly  Cys  Gly  Gly  Asn  Arg  Asn  Asn  Phe
              35                        40                            45

Asp  Thr  Glu  Glu  Tyr  Cys  Ala  Ala  Val  Cys  Gly  Ser  Ala
              50                        55              58
```

( 2 ) INFORMATION FOR SEQ ID NO:44:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:44:

```
Val  Arg  Glu  Val  Cys  Ser  Glu  Gln  Ala  Glu  Pro  Gly  Trp  Cys  Arg
 1              5                        10                            15

Ala  Leu  Ile  Leu  Arg  Trp  Tyr  Phe  Asp  Val  Thr  Glu  Gly  Lys  Cys
              20                        25                            30

Ala  Pro  Phe  Phe  Tyr  Gly  Gly  Cys  Gly  Gly  Asn  Arg  Asn  Asn  Phe
              35                        40                            45

Asp  Thr  Glu  Glu  Tyr  Cys  Ala  Ala  Val  Cys  Gly  Ser  Ala
              50                        55              58
```

( 2 ) INFORMATION FOR SEQ ID NO:45:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:45:

```
Val  Arg  Glu  Val  Cys  Ser  Glu  Gln  Ala  Glu  Pro  Gly  Phe  Cys  Arg
 1              5                        10                            15

Ala  Leu  Ile  Leu  Arg  Trp  Tyr  Phe  Asp  Val  Thr  Glu  Gly  Lys  Cys
              20                        25                            30

Ala  Pro  Phe  Phe  Tyr  Gly  Gly  Cys  Gly  Gly  Asn  Arg  Asn  Asn  Phe
              35                        40                            45

Asp  Thr  Glu  Glu  Tyr  Cys  Ala  Ala  Val  Cys  Gly  Ser  Ala
              50                        55              58
```

( 2 ) INFORMATION FOR SEQ ID NO:46:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:46:

```
Val  Arg  Glu  Val  Cys  Ser  Glu  Gln  Ala  Glu  Gly  Gly  Trp  Cys  Arg
 1              5                        10                            15
```

```
Ala  Leu  Ile  Leu  Arg  Trp  Tyr  Phe  Asp  Val  Thr  Glu  Gly  Lys  Cys
              20                          25                           30

Ala  Pro  Phe  Phe  Tyr  Gly  Gly  Cys  Gly  Gly  Asn  Arg  Asn  Asn  Phe
              35                          40                           45

Asp  Thr  Glu  Glu  Tyr  Cys  Ala  Ala  Val  Cys  Gly  Ser  Ala
              50                          55              58
```

( 2 ) INFORMATION FOR SEQ ID NO:47:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:47:

```
Val  Arg  Glu  Val  Cys  Ser  Glu  Gln  Ala  Glu  Pro  Gly  Pro  Cys  Arg
 1                     5                         10                    15

Ala  Met  Ile  Ser  Arg  Trp  Tyr  Phe  Asp  Val  Thr  Glu  Gly  Lys  Cys
              20                          25                           30

Ala  Pro  Phe  Phe  Tyr  Gly  Gly  Cys  Tyr  Gly  Asn  Arg  Asn  Asn  Phe
              35                          40                           45

Asp  Thr  Glu  Glu  Tyr  Cys  Ala  Ala  Val  Cys  Gly  Ser  Ala
              50                          55              58
```

( 2 ) INFORMATION FOR SEQ ID NO:48:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:48:

```
Val  Arg  Glu  Val  Cys  Ser  Glu  Gln  Ala  Glu  Pro  Gly  Trp  Cys  Arg
 1                     5                         10                    15

Ala  Met  Ile  Ser  Arg  Trp  Tyr  Phe  Asp  Val  Thr  Glu  Gly  Lys  Cys
              20                          25                           30

Ala  Pro  Phe  Ile  Tyr  Gly  Gly  Cys  Gly  Gly  Asn  Arg  Asn  Asn  Phe
              35                          40                           45

Asp  Thr  Glu  Glu  Tyr  Cys  Ala  Ala  Val  Cys  Gly  Ser  Ala
              50                          55              58
```

( 2 ) INFORMATION FOR SEQ ID NO:49:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:49:

```
Val  Arg  Glu  Val  Cys  Ser  Glu  Gln  Ala  Glu  Pro  Gly  Pro  Cys  Lys
 1                     5                         10                    15

Ala  Met  Ile  Ser  Arg  Trp  Tyr  Phe  Asp  Val  Thr  Glu  Gly  Lys  Cys
              20                          25                           30

Ala  Pro  Phe  Ile  Tyr  Gly  Gly  Cys  Trp  Gly  Asn  Arg  Asn  Asn  Phe
              35                          40                           45

Asp  Thr  Glu  Glu  Tyr  Cys  Ala  Ala  Val  Cys  Gly  Ser  Ala
              50                          55              58
```

( 2 ) INFORMATION FOR SEQ ID NO:50:

( i ) SEQUENCE CHARACTERISTICS:
        ( A ) LENGTH: 58 amino acids (B) TYPE: Amino Acid
(D) TOPOLOGY: Linear (xi) SEQUENCE DESCRIPTION: SEQ ID NO:50:

| Val | Arg | Glu | Val | Cys | Ser | Glu | Gln | Ala | Glu | Thr | Gly | Pro | Cys | Arg |
|---|---|---|---|---|---|---|---|---|---|---|---|---|---|---|
| 1 | | | | 5 | | | | | 10 | | | | | 15 |

| Ala | Leu | Ile | Ser | Arg | Trp | Tyr | Phe | Asp | Val | Thr | Glu | Gly | Lys | Cys |
|---|---|---|---|---|---|---|---|---|---|---|---|---|---|---|
| | | | | 20 | | | | | 25 | | | | | 30 |

| Ala | Pro | Phe | Trp | Tyr | Gly | Gly | Cys | Gly | Gly | Asn | Arg | Asn | Asn | Phe |
|---|---|---|---|---|---|---|---|---|---|---|---|---|---|---|
| | | | | 35 | | | | | 40 | | | | | 45 |

| Asp | Thr | Glu | Glu | Tyr | Cys | Ala | Ala | Val | Cys | Gly | Ser | Ala |
|---|---|---|---|---|---|---|---|---|---|---|---|---|
| | | | | 50 | | | | | 55 | | | 58 |

(2) INFORMATION FOR SEQ ID NO:51:

(i) SEQUENCE CHARACTERISTICS:
(A) LENGTH: 58 amino acids
(B) TYPE: Amino Acid
(D) TOPOLOGY: Linear (xi) SEQUENCE DESCRIPTION: SEQ ID NO:51:

| Val | Arg | Glu | Val | Cys | Ser | Glu | Gln | Ala | Glu | Thr | Gly | Pro | Cys | Arg |
|---|---|---|---|---|---|---|---|---|---|---|---|---|---|---|
| 1 | | | | 5 | | | | | 10 | | | | | 15 |

| Ala | Leu | Ile | Ser | Arg | Trp | Tyr | Phe | Asp | Val | Thr | Glu | Gly | Lys | Cys |
|---|---|---|---|---|---|---|---|---|---|---|---|---|---|---|
| | | | | 20 | | | | | 25 | | | | | 30 |

| Ala | Pro | Phe | Tyr | Tyr | Gly | Gly | Cys | Gly | Gly | Asn | Arg | Asn | Asn | Phe |
|---|---|---|---|---|---|---|---|---|---|---|---|---|---|---|
| | | | | 35 | | | | | 40 | | | | | 45 |

| Asp | Thr | Glu | Glu | Tyr | Cys | Ala | Ala | Val | Cys | Gly | Ser | Ala |
|---|---|---|---|---|---|---|---|---|---|---|---|---|
| | | | | 50 | | | | | 55 | | | 58 |

(2) INFORMATION FOR SEQ ID NO:52:

(i) SEQUENCE CHARACTERISTICS:
(A) LENGTH: 58 amino acids
(B) TYPE: Amino Acid
(D) TOPOLOGY: Linear (xi) SEQUENCE DESCRIPTION: SEQ ID NO:52:

| Val | Arg | Glu | Val | Cys | Ser | Glu | Gln | Ala | Glu | Pro | Gly | Val | Cys | Arg |
|---|---|---|---|---|---|---|---|---|---|---|---|---|---|---|
| 1 | | | | 5 | | | | | 10 | | | | | 15 |

| Ala | Leu | Ile | Leu | Arg | Trp | Tyr | Phe | Asp | Val | Thr | Glu | Gly | Lys | Cys |
|---|---|---|---|---|---|---|---|---|---|---|---|---|---|---|
| | | | | 20 | | | | | 25 | | | | | 30 |

| Ala | Pro | Phe | Phe | Tyr | Gly | Gly | Cys | Tyr | Gly | Asn | Arg | Asn | Asn | Phe |
|---|---|---|---|---|---|---|---|---|---|---|---|---|---|---|
| | | | | 35 | | | | | 40 | | | | | 45 |

| Asp | Thr | Glu | Glu | Tyr | Cys | Ala | Ala | Val | Cys | Gly | Ser | Ala |
|---|---|---|---|---|---|---|---|---|---|---|---|---|
| | | | | 50 | | | | | 55 | | | 58 |

(2) INFORMATION FOR SEQ ID NO:53:

(i) SEQUENCE CHARACTERISTICS:
(A) LENGTH: 58 amino acids
(B) TYPE: Amino Acid
(D) TOPOLOGY: Linear (xi) SEQUENCE DESCRIPTION: SEQ ID NO:53:

| Val | Arg | Glu | Val | Cys | Ser | Glu | Gln | Ala | Glu | Pro | Gly | Leu | Cys | Arg |
|---|---|---|---|---|---|---|---|---|---|---|---|---|---|---|
| 1 | | | | 5 | | | | | 10 | | | | | 15 |

| Ala | Leu | Ile | Ser | Arg | Trp | Tyr | Phe | Asp | Val | Thr | Glu | Gly | Lys | Cys |
|---|---|---|---|---|---|---|---|---|---|---|---|---|---|---|
| | | | | 20 | | | | | 25 | | | | | 30 |

| Ala | Pro | Phe | Phe | Tyr | Gly | Gly | Cys | Tyr | Gly | Asn | Arg | Asn | Asn | Phe |
|---|---|---|---|---|---|---|---|---|---|---|---|---|---|---|
| | | | | 35 | | | | | 40 | | | | | 45 |

```
Asp  Thr  Glu  Glu  Tyr  Cys  Ala  Ala  Val  Cys  Gly  Ser  Ala
               50                       55                  58
```

( 2 ) INFORMATION FOR SEQ ID NO:54:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:54:

```
Val  Arg  Glu  Val  Cys  Ser  Glu  Gln  Ala  Glu  Pro  Gly  Trp  Cys  Arg
 1             5                       10                            15

Ala  Leu  Ile  Leu  Arg  Trp  Tyr  Phe  Asp  Val  Thr  Glu  Gly  Lys  Cys
               20                       25                            30

Ala  Pro  Phe  Phe  Tyr  Gly  Gly  Cys  Tyr  Gly  Asn  Arg  Asn  Asn  Phe
               35                       40                            45

Asp  Thr  Glu  Glu  Tyr  Cys  Ala  Ala  Val  Cys  Gly  Ser  Ala
               50                       55                  58
```

( 2 ) INFORMATION FOR SEQ ID NO:55:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:55:

```
Val  Arg  Glu  Val  Cys  Ser  Glu  Gln  Ala  Glu  Pro  Gly  Pro  Cys  Arg
 1             5                       10                            15

Ala  Leu  Ile  Leu  Arg  Trp  Tyr  Phe  Asp  Val  Thr  Glu  Gly  Lys  Cys
               20                       25                            30

Ala  Pro  Phe  Phe  Tyr  Gly  Gly  Cys  Gly  Gly  Asn  Arg  Asn  Asn  Phe
               35                       40                            45

Asp  Thr  Glu  Glu  Tyr  Cys  Ala  Ala  Val  Cys  Gly  Ser  Ala
               50                       55                  58
```

( 2 ) INFORMATION FOR SEQ ID NO:56:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:56:

```
Val  Arg  Glu  Val  Cys  Ser  Glu  Gln  Ala  Glu  Pro  Gly  Pro  Cys  Arg
 1             5                       10                            15

Ala  Met  Met  Lys  Arg  Trp  Tyr  Phe  Asp  Val  Thr  Glu  Gly  Lys  Cys
               20                       25                            30

Ala  Pro  Phe  Ile  Tyr  Gly  Gly  Cys  His  Gly  Asn  Arg  Asn  Asn  Phe
               35                       40                            45

Asp  Thr  Glu  Glu  Tyr  Cys  Ala  Ala  Val  Cys  Gly  Ser  Ala
               50                       55                  58
```

( 2 ) INFORMATION FOR SEQ ID NO:57:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:57:

```
Val  Arg  Glu  Val  Cys  Ser  Glu  Gln  Ala  Glu  Pro  Gly  Pro  Cys  Arg
```

```
              1               5                    10                   15
         Ala  Leu  Met  Lys  Arg  Trp  Tyr  Phe  Asp  Val  Thr  Glu  Gly  Lys  Cys
                             20                  25                            30

Ala  Pro  Phe  Val  Tyr  Gly  Gly  Cys  Tyr  Gly  Asn  Arg  Asn  Asn  Phe
                             35                  40                            45

Asp  Thr  Glu  Glu  Tyr  Cys  Ala  Ala  Val  Cys  Gly  Ser  Ala
                             50                  55             58
```

( 2 ) INFORMATION FOR SEQ ID NO:58:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:58:

```
         Val  Arg  Glu  Val  Cys  Ser  Glu  Gln  Ala  Glu  Pro  Gly  Pro  Cys  Arg
         1                  5                   10                            15

Ala  Leu  Met  Lys  Arg  Trp  Tyr  Phe  Asp  Val  Thr  Glu  Gly  Lys  Cys
                             20                  25                            30

Ala  Pro  Phe  Val  Tyr  Gly  Gly  Cys  Phe  Gly  Asn  Arg  Asn  Asn  Phe
                             35                  40                            45

Asp  Thr  Glu  Glu  Tyr  Cys  Ala  Ala  Val  Cys  Gly  Ser  Ala
                             50                  55             58
```

( 2 ) INFORMATION FOR SEQ ID NO:59:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:59:

```
         Val  Arg  Glu  Val  Cys  Ser  Glu  Gln  Ala  Glu  Pro  Gly  Pro  Cys  Arg
         1                  5                   10                            15

Ala  Leu  Met  Lys  Arg  Trp  Tyr  Phe  Asp  Val  Thr  Glu  Gly  Lys  Cys
                             20                  25                            30

Ala  Pro  Phe  Ile  Tyr  Gly  Gly  Cys  Tyr  Gly  Asn  Arg  Asn  Asn  Phe
                             35                  40                            45

Asp  Thr  Glu  Glu  Tyr  Cys  Ala  Ala  Val  Cys  Gly  Ser  Ala
                             50                  55             58
```

( 2 ) INFORMATION FOR SEQ ID NO:60:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:60:

```
         Val  Arg  Glu  Val  Cys  Ser  Glu  Gln  Ala  Glu  Pro  Gly  Pro  Cys  Arg
         1                  5                   10                            15

Ala  Met  Tyr  Lys  Arg  Trp  Tyr  Phe  Asp  Val  Thr  Glu  Gly  Lys  Cys
                             20                  25                            30

Ala  Pro  Phe  Ile  Tyr  Gly  Gly  Cys  Tyr  Gly  Asn  Arg  Asn  Asn  Phe
                             35                  40                            45

Asp  Thr  Glu  Glu  Tyr  Cys  Ala  Ala  Val  Cys  Gly  Ser  Ala
                             50                  55             58
```

( 2 ) INFORMATION FOR SEQ ID NO:61:

(i) SEQUENCE CHARACTERISTICS:
    (A) LENGTH: 58 amino acids
    (B) TYPE: Amino Acid
    (D) TOPOLOGY: Linear (xi) SEQUENCE DESCRIPTION: SEQ ID NO:61:

```
Val Arg Glu Val Cys Ser Glu Gln Ala Glu Pro Gly Val Cys Arg
 1               5                  10                  15

Ala Met Met Lys Arg Trp Tyr Phe Asp Val Thr Glu Gly Lys Cys
                20                  25                  30

Ala Pro Phe Ile Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

(2) INFORMATION FOR SEQ ID NO:62:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:62:

```
Val Arg Glu Val Cys Ser Glu Gln Ala Glu Pro Gly Pro Cys Lys
 1               5                  10                  15

Ala Leu Met Arg Arg Trp Tyr Phe Asp Val Thr Glu Gly Lys Cys
                20                  25                  30

Ala Pro Phe Tyr Tyr Gly Gly Cys Tyr Gly Asn Arg Asn Asn Phe
                35                  40                  45

Asp Thr Glu Glu Tyr Cys Ala Ala Val Cys Gly Ser Ala
                50                  55          58
```

(2) INFORMATION FOR SEQ ID NO:63:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:63:

```
Val Arg Glu Val Cys Ser Glu Gln Ala Glu Pro Gly Pro Cys Lys
 1               5                  10                  15

Ala Ile Met Lys Arg Trp Tyr Phe Asp Val Thr Glu Gly Lys Cys
                20                  25                  30

Ala Pro Phe Ile Tyr Gly Gly Cys His Gly Asn Arg Asn Asn Phe
                35                  40                  45

Asp Thr Glu Glu Tyr Cys Ala Ala Val Cys Gly Ser Ala
                50                  55          58
```

(2) INFORMATION FOR SEQ ID NO:64:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:64:

```
Val Arg Glu Val Cys Ser Glu Gln Ala Glu Pro Gly Pro Cys Lys
 1               5                  10                  15

Ala Leu Met Lys Arg Trp Tyr Phe Asp Val Thr Glu Gly Lys Cys
                20                  25                  30

Ala Pro Phe Tyr Tyr Gly Gly Cys His Gly Asn Arg Asn Asn Phe
```

35                            40                              45

Asp  Thr  Glu  Glu  Tyr  Cys  Ala  Ala  Val  Cys  Gly  Ser  Ala
                      50                            55              58

( 2 ) INFORMATION FOR SEQ ID NO:65:

( i ) SEQUENCE CHARACTERISTICS:
            ( A ) LENGTH: 58 amino acids
            ( B ) TYPE: Amino Acid
            ( D ) TOPOLOGY: Linear ( x i ) SEQUENCE DESCRIPTION: SEQ ID NO:65:

Val  Arg  Glu  Val  Cys  Ser  Glu  Gln  Ala  Glu  Pro  Gly  Pro  Cys  Lys
 1                    5                           10                         15

Ala  Leu  Met  Lys  Arg  Trp  Tyr  Phe  Asp  Val  Thr  Glu  Gly  Lys  Cys
                      20                          25                         30

Ala  Pro  Phe  Trp  Tyr  Gly  Gly  Cys  Trp  Gly  Asn  Arg  Asn  Asn  Phe
                      35                          40                         45

Asp  Thr  Glu  Glu  Tyr  Cys  Ala  Ala  Val  Cys  Gly  Ser  Ala
                      50                          55              58

( 2 ) INFORMATION FOR SEQ ID NO:66:

( i ) SEQUENCE CHARACTERISTICS:
            ( A ) LENGTH: 58 amino acids
            ( B ) TYPE: Amino Acid
            ( D ) TOPOLOGY: Linear ( x i ) SEQUENCE DESCRIPTION: SEQ ID NO:66:

Val  Arg  Glu  Val  Cys  Ser  Glu  Gln  Ala  Glu  Pro  Gly  Pro  Cys  Lys
 1                    5                           10                         15

Ala  Met  Ile  Lys  Arg  Trp  Tyr  Phe  Asp  Val  Thr  Glu  Gly  Lys  Cys
                      20                          25                         30

Ala  Pro  Phe  Leu  Tyr  Gly  Gly  Cys  Tyr  Gly  Asn  Arg  Asn  Asn  Phe
                      35                          40                         45

Asp  Thr  Glu  Glu  Tyr  Cys  Ala  Ala  Val  Cys  Gly  Ser  Ala
                      50                          55              58

( 2 ) INFORMATION FOR SEQ ID NO:67:

( i ) SEQUENCE CHARACTERISTICS:
            ( A ) LENGTH: 58 amino acids
            ( B ) TYPE: Amino Acid
            ( D ) TOPOLOGY: Linear ( x i ) SEQUENCE DESCRIPTION: SEQ ID NO:67:

Val  Arg  Glu  Val  Cys  Ser  Glu  Gln  Ala  Glu  Pro  Gly  Pro  Cys  Lys
 1                    5                           10                         15

Ala  Leu  Met  Lys  Arg  Trp  Tyr  Phe  Asp  Val  Thr  Glu  Gly  Lys  Cys
                      20                          25                         30

Ala  Pro  Phe  Phe  Tyr  Gly  Gly  Cys  Tyr  Gly  Asn  Arg  Asn  Asn  Phe
                      35                          40                         45

Asp  Thr  Glu  Glu  Tyr  Cys  Ala  Ala  Val  Cys  Gly  Ser  Ala
                      50                          55              58

( 2 ) INFORMATION FOR SEQ ID NO:68:

( i ) SEQUENCE CHARACTERISTICS:
            ( A ) LENGTH: 58 amino acids
            ( B ) TYPE: Amino Acid
            ( D ) TOPOLOGY: Linear ( x i ) SEQUENCE DESCRIPTION: SEQ ID NO:68:

Val  Arg  Glu  Val  Cys  Ser  Glu  Gln  Ala  Glu  Pro  Gly  Pro  Cys  Lys
1                  5                       10                            15

Ala  Leu  Met  Lys  Arg  Trp  Tyr  Phe  Asp  Val  Thr  Glu  Gly  Lys  Cys
                    20                       25                           30

Ala  Pro  Phe  Tyr  Tyr  Gly  Gly  Cys  Tyr  Gly  Asn  Arg  Asn  Asn  Phe
                    35                       40                           45

Asp  Thr  Glu  Glu  Tyr  Cys  Ala  Ala  Val  Cys  Gly  Ser  Ala
                    50                       55              58

( 2 ) INFORMATION FOR SEQ ID NO:69:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:69:

Val  Arg  Glu  Val  Cys  Ser  Glu  Gln  Ala  Glu  Pro  Gly  Pro  Cys  Lys
1                  5                       10                            15

Ala  Leu  Met  Lys  Arg  Trp  Tyr  Phe  Asp  Val  Thr  Glu  Gly  Lys  Cys
                    20                       25                           30

Ala  Pro  Phe  Val  Tyr  Gly  Gly  Cys  Tyr  Gly  Asn  Arg  Asn  Asn  Phe
                    35                       40                           45

Asp  Thr  Glu  Glu  Tyr  Cys  Ala  Ala  Val  Cys  Gly  Ser  Ala
                    50                       55              58

( 2 ) INFORMATION FOR SEQ ID NO:70:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:70:

Val  Arg  Glu  Val  Cys  Ser  Glu  Gln  Ala  Glu  Pro  Gly  Ala  Cys  Lys
1                  5                       10                            15

Ala  Met  Tyr  Lys  Arg  Trp  Tyr  Phe  Asp  Val  Thr  Glu  Gly  Lys  Cys
                    20                       25                           30

Ala  Pro  Phe  Ile  Tyr  Gly  Gly  Cys  Gly  Gly  Asn  Arg  Asn  Asn  Phe
                    35                       40                           45

Asp  Thr  Glu  Glu  Tyr  Cys  Ala  Ala  Val  Cys  Gly  Ser  Ala
                    50                       55              58

( 2 ) INFORMATION FOR SEQ ID NO:71:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:71:

Val  Arg  Glu  Val  Cys  Ser  Glu  Gln  Ala  Glu  Pro  Gly  Pro  Gly  Arg
1                  5                       10                            15

Ala  Leu  Ile  Leu  Arg  Trp  Tyr  Phe  Asp  Val  Thr  Glu  Gly  Lys  Cys
                    20                       25                           30

Ala  Pro  Phe  Phe  Tyr  Gly  Gly  Ala  Tyr  Gly  Asn  Arg  Asn  Asn  Phe
                    35                       40                           45

Asp  Thr  Glu  Glu  Tyr  Cys  Ala  Ala  Val  Cys  Gly  Ser  Ala
                    50                       55              58

(2) INFORMATION FOR SEQ ID NO:72:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:72:

```
Val Arg Glu Val Cys Ser Glu Gln Ala Glu Pro Gly Pro Cys Arg
 1               5                  10                   15

Ala Leu Ile Leu Arg Trp Tyr Phe Asp Val Thr Glu Gly Lys Cys
                20                  25                   30

Ala Pro Phe Phe Tyr Gly Gly Cys Tyr Gly Asn Arg Asn Asn Phe
                35                  40                   45

Asp Thr Glu Glu Tyr Cys Ala Ala Val Cys Gly Ser Ala
                50                  55       58
```